(12) United States Patent
Scibona et al.

(10) Patent No.: US 7,355,685 B2
(45) Date of Patent: Apr. 8, 2008

(54) STROBOSCOPIC LED LIGHT SOURCE FOR BLOOD PROCESSING APPARATUS

(75) Inventors: Joseph A. Scibona, Littleton, CO (US); Shannon Durkee, Phoenix, AZ (US)

(73) Assignee: Gambro BCT, Inc., Lakewood, CO (US)

(*) Notice: Subject to any disclaimer, the term of this patent is extended or adjusted under 35 U.S.C. 154(b) by 0 days.

(21) Appl. No.: 11/867,816

(22) Filed: Oct. 5, 2007

(65) Prior Publication Data
US 2008/0024757 A1 Jan. 31, 2008

Related U.S. Application Data

(60) Division of application No. 10/905,353, filed on Dec. 29, 2004, now Pat. No. 7,327,443, which is a continuation-in-part of application No. 10/884,877, filed on Jul. 1, 2004.

(60) Provisional application No. 60/485,015, filed on Jul. 2, 2003.

(51) Int. Cl.
*G01N 33/48* (2006.01)
(52) U.S. Cl. .................... 356/39
(58) Field of Classification Search .............. 356/39; 422/44
See application file for complete search history.

(56) References Cited

U.S. PATENT DOCUMENTS 5,741,213 A * 4/1998 Kouchi et al. ............. 600/310

5,930,033 A 7/1999 Inoue et al.
2002/0196435 A1 12/2002 Cohen et al.

FOREIGN PATENT DOCUMENTS

JP 04 371245 12/1992
WO WO 2005/003738 1/2005

OTHER PUBLICATIONS

International Search Report and Written Opinion for PCT/US2005/033219, Jun. 6, 2006.
International Search Report on Patentability, for PCT/US2005/033219, Jul. 12, 2007.

* cited by examiner

*Primary Examiner*—Roy M Punnoose
(74) *Attorney, Agent, or Firm*—John R. Merkling; Edna M. O'Connor; Laura B. Arciniega

(57) ABSTRACT

The invention relates to apparatus for controlling the processing of blood into blood components, particularly components for stroboscopic LED light sources for centrifuges. The stroboscopic apparatus comprises a first light source with reflective surfaces spaced around a central illumination axis, and light-emitting diodes spaced away from the axis radially outward from the reflective surfaces. An additional light source comprises a modified parabolic reflector surrounding a light emitting diode, the parabolic reflector having walls spaced outwardly from an axis of symmetry such that focal points fall radially outwardly from a center of the LED, forming a circular focal area. A controller that energizes the diodes for selected periods of time comprises a pair of switches connected in series, with an LED connected between the switches. One of the switches is connected to ground and is closed at the end of a period of illumination.

14 Claims, 19 Drawing Sheets

STROBOSCOPIC LED LIGHT SOURCE FOR BLOOD PROCESSING APPARATUS

CROSS-REFERENCE TO RELATED APPLICATIONS

This application is a divisional of U.S. application Ser. No. 10/905,353, filed Dec. 29, 2004, which is a continuation-in-part of U.S. application Ser. No. 10/884,877, filed Jul. 1, 2004, which claims the benefit of U.S. Provisional Application No. 60/485,015, filed Jul. 2, 2003.

BACKGROUND OF INVENTION

Blood collection and processing play important roles in the worldwide health care system. In conventional blood collection, blood is removed from a donor or patient, separated into its various blood components via centrifugation, filtration and/or elutriation and stored in sterile containers for future infusion into a patient for therapeutic use. The separated blood components typically include fractions corresponding to red blood cells, white blood cells, platelets and plasma. Separation of blood into its components can be performed continuously during collection or can be performed subsequent to collection in batches, particularly with respect to the processing of whole blood samples. Separation of blood into its various components under highly sterile conditions is critical to most therapeutic applications.

Recently, apheresis blood collection techniques have been adopted in many blood collection centers wherein a selected component of blood is collected and the balance of the blood is returned to the donor during collection. In apheresis, blood is removed from a donor and immediately separated into its components by on-line blood processing methods. Typically, on-line blood processing is provided by density centrifugation, filtration and/or diffusion-based separation techniques. One or more of the separated blood components are collected and stored in sterile containers, while the remaining blood components are directly re-circulated to the donor. An advantage of this method is that it allows more frequent donation from an individual donor because only a selected blood component is collected and purified. For example, a donor undergoing plateletpheresis, whereby platelets are collected and the non-platelet blood components are returned to the donor, may donate blood as often as once every fourteen days.

Apheresis blood processing also plays an important role in a large number of therapeutic procedures. In these methods, blood is withdrawn from a patient undergoing therapy, separated, and a selected fraction is collected while the remainder is returned to the patient. For example, a patient may undergo leukapheresis prior to radiation therapy, whereby the white blood cell component of his blood is separated, collected and stored to avoid exposure to radiation. Alternatively, apheresis techniques may be used to perform red blood cell exchange for patients with hematological disorders such as sickle cell anemia and thalassemia, whereby a patient's red blood cell component is removed and donated packed red blood cells are provided to the patient along with his remaining blood components. Further, apheresis may be used to perform therapeutic platelet depletion for patients having thrombocytosis and therapeutic plasma exchange for patients with autoimmune diseases.

Both conventional blood collection and apheresis systems typically employ differential centrifugation methods for separating blood into its various blood components. In differential centrifugation, blood is circulated through a sterile separation chamber, which is rotated at high rotational speeds about a central rotation axis. Rotation of the separation chamber creates a centrifugal force directed along rotating axes of separation oriented perpendicular to the central rotation axis of the centrifuge. The centrifugal force generated upon rotation separates particles suspended in the blood sample into discrete fractions having different densities. Specifically, a blood sample separates into discrete phases corresponding to a higher density fraction comprising red blood cells and a lower density fraction comprising plasma. In addition, an intermediate density fraction comprising platelets and leukocytes forms an interface layer between the red blood cells and the plasma. Descriptions of blood centrifugation devices are provided in U.S. Pat. No. 5,653,887 and U.S. patent application Ser. No. 10/413,890.

To achieve continuous, high throughput blood separation, extraction or collection ports are provided in most separation chambers. Extraction ports are capable of withdrawing material from the separation chamber at adjustable flow rates and, typically, are disposed at selected positions along the separation axis corresponding to discrete blood components. To ensure the extracted fluid exiting a selected extraction port is substantially limited to a single phase, however, the phase boundaries between the separated blood components must be positioned along the separation axis such that an extraction port contacts a single phase. For example, if the fraction containing white blood cells resides too close to the extraction port corresponding to platelet enriched plasma, white blood cells may enter the platelet enriched plasma stream exiting the separation chamber, thereby degrading the extent of separation achieved during blood processing. Although conventional blood processing via density centrifugation is capable of efficient separation of individual blood components, the purities of individual components obtained using this method is often not optimal for use in many therapeutic applications. For example, centrifugation separation of blood samples is unable to consistently (99% of the time) produce separated platelet components which have less than $1 \times 10^6$ white blood cells per every $3 \times 10^{11}$ platelets collected. The presence of white blood cells in platelet products increases the risks of viral exposure and immunological complications upon infusion into a patient.

The purity of extracted blood components using density centrifugation is currently limited by the control of the position of phase boundary layers between separated components provided by conventional centrifugation devices and methods. The position of phase boundaries along the separation axis depends on a number of variables. First, phase boundary positions depend on the relative flow rates of individual blood components out of the separation chamber. Second, phase boundary positions depend on the rotational velocity of the separation chamber about the central rotation axis and the temperature of the blood undergoing separation. Third, phase boundary positions vary with the composition of the blood undergoing processing. Blood sample composition may vary considerably from donor to donor and/or from patient to patient. In addition, blood composition may vary significantly as function of time for a given donor or patient, especially as blood is recycled through the separation chamber multiple times. Given the sensitivity of the phase boundary position to many variables, which change from person to person and during processing, it is important to monitor the position of the phase boundaries during blood processing to ensure optimal separation conditions are maintained and the desired purity of selected blood components is achieved. In addition, accurate characterization of the positions of phase boundaries allows for separation conditions to be adjusted and optimized for changes in blood composition during processing.

It will be appreciated from the foregoing that a need exists for methods and devices for monitoring and controlling the processing of whole blood samples and blood component samples. Particularly, optical monitoring methods and devices are needed which are capable of accurately characterizing the separation, extraction and collection of blood components processed by density centrifugation, including providing controlled stroboscopic light sources with consistent duration and intensity of illumination.

SUMMARY OF THE INVENTION

This invention provides stroboscopic LED light sources for use with devices for improving the processing of fluids, such as blood, components of blood and fluids derived from blood.

In one aspect, this invention provides methods, devices and device components for improving the separation of whole blood via density centrifugation and subsequent collection of selected, separated blood components. Particularly, the invention relates to optical methods, devices and device components for stroboscopic light sources for light to be transmitted and/or scattered by separated blood components in a rotating separation chamber, particularly a separation chamber having an optical cell with one or more extraction ports.

The invention relates to apparatus for controlling the processing of blood into blood components, particularly components for stroboscopic LED light sources for centrifuges. The stroboscopic apparatus comprises a first light source with reflective surfaces spaced around a central illumination axis, and light-emitting diodes spaced away from the axis radially outward from the reflective surfaces. An additional light source comprises a modified parabolic reflector surrounding a light emitting diode, the parabolic reflector having walls spaced outwardly from an axis of symmetry such that focal points fall radially outwardly from a center of the LED, forming a circular focal area. A controller that energizes the diodes for selected periods of time comprises a pair of switches connected in series, with an LED connected between the switches. One of the switches is connected to ground and is closed at the end of a period of illumination.

An exemplary optical monitoring system for a density centrifuge having a separation chamber rotating about a central rotation axis comprises at least one light source, a light collection element and a detector. Rotation of the separation chamber about a central rotation axis results in separation of the blood components in the separation chamber according to density along rotating separation axes oriented perpendicular to the central rotation axis of the centrifuge. Both the light source and light collection element are arranged such that they are periodically in optical communication with an observation region positioned on the density centrifuge. In one embodiment, the light source and detector are arranged such that an optical cell of the separation chamber is periodically rotated into and out of the observation region. The light source is capable of providing an incident light beam which illuminates at least a portion of the density centrifuge, preferably an optical cell of the rotating separation chamber, thereby generating light which is transmitted, scattered, or both, by blood components undergoing separation. Preferred light sources are capable of generating an incident light beam having a selected wavelength range including, but not limited to, visible light, infrared light and/or ultraviolet light. In one embodiment, a plurality of light sources are provided capable of illuminating a plurality of sides of an optical cell of a separation chamber.

The light collection element is capable of collecting light from an observation region. In one embodiment, collected light from the observation region corresponds to light which is transmitted and/or scattered by blood components undergoing separation, light which is transmitted and/or scattered by components of the centrifugation device, such as the separation chamber, or both. The light collection element directs the collected light onto the detector. The detector may also be capable of generating one or more output signals corresponding to the distribution of transmitted and/or scattered light intensities from the observation region. The output signal may be transmitted to a device, such as a computer, capable of displaying the distribution of intensities, storing the distribution of intensities and/or processing the distribution of intensities.

The invention is further illustrated by the following description, examples, drawings and claims.

DETAILED DESCRIPTION OF THE INVENTION

Figure 1:
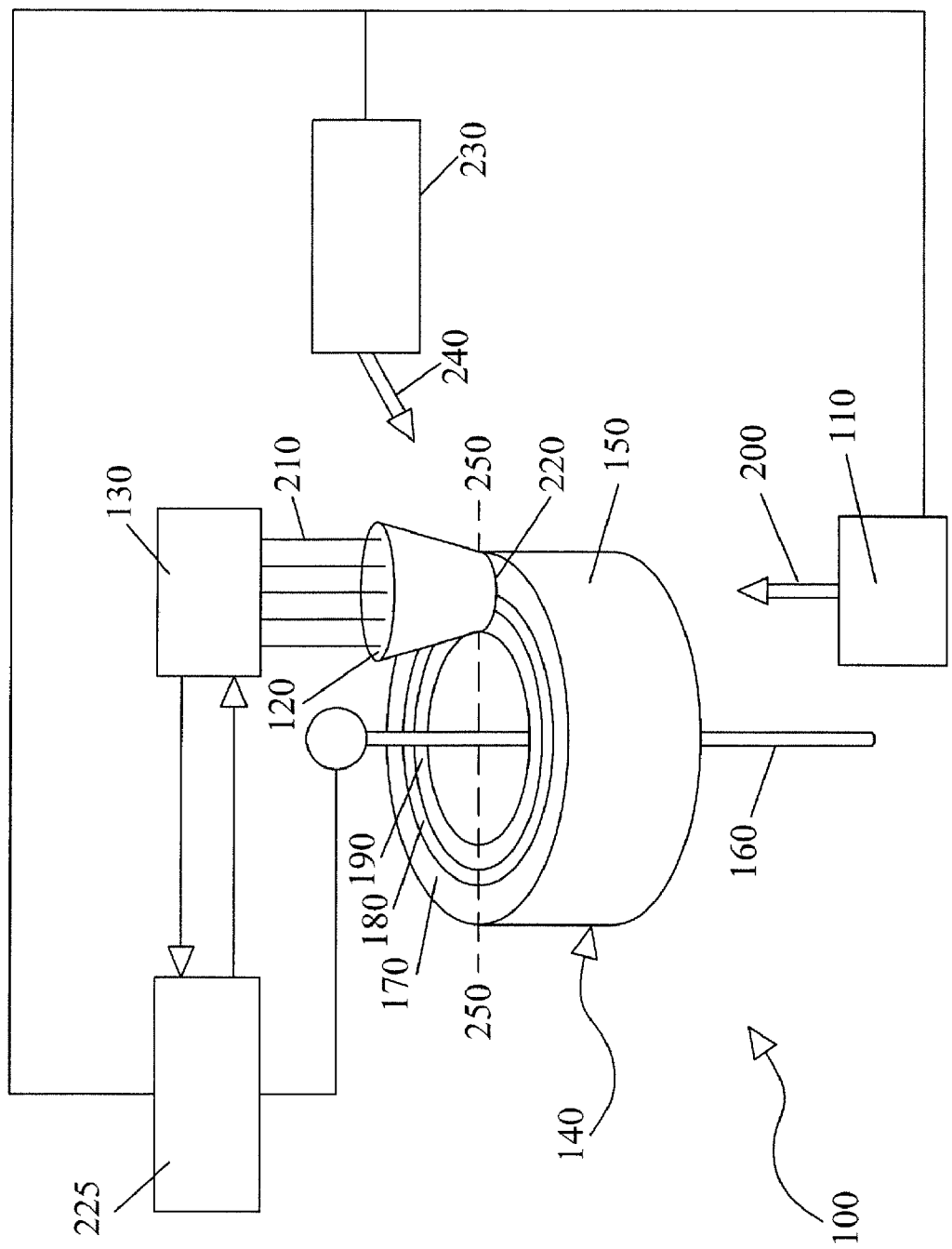
FIG. 1 is a schematic drawing showing an optical monitoring and control system of the present invention.

Referring to the drawings, like numerals indicate like elements and the same number appearing in more than one drawing refers to the same element. In addition, hereinafter, the following definitions apply:

The terms "light" and "electromagnetic radiation" are used synonymously and refer to waves of electric and magnetic fields that also exhibit particle-like behavior. Light useful for the methods of the present invention includes gamma rays, X-rays, ultraviolet light, visible light, infrared light, microwaves, radio waves or any combination of these.

"Light collection element" refers to a device or device component that collects light and distributes the collected light in a desired way. Light collection elements useable in the present invention are capable of collecting at least a portion of transmitted light, scattered light or both generated upon illumination of an observation region on a blood-processing device. Exemplary light collection elements of the present invention are capable of collecting light in a manner generating an image of an observation region on a detector. Light collection elements of the present invention include, but are not limited to, fixed focus lenses, spherical lenses, cylindrical lenses, aspheric lenses, wide angle lenses, zoom lenses, concave lenses, convex lenses, biconcave lenses, biconvex lenses, lens systems comprising a plurality of lenses, wave guides, fiber optic couplers, reflectors, spherical mirrors, aspherical mirrors, prisms, apertures, lenses, or any combination or equivalents of these. Light collection elements of the present invention are capable of directing collected light onto another optical device or device component, such as a detector. Light collection elements include at least one lens system having a selectively adjustable field of view and/or focal length. Light collection elements can be translatable along a detection axis, which is perpendicular to a central rotation axis.

"Field of view" refers to the angular distribution of light rays, which are collected and detected by an optical detection system, such as a light collection element in optical communication with a detector. Optical detection systems of the present invention can have a fixed field of view or a field of view, which is selectively adjustable.

"Blood processing" refers to the manipulation of a blood sample or component thereof, to realize a change in composition. Blood processing includes methods of separating blood or a component thereof into components or subcomponents, leukoreduction, pathogen inactivation, blood filtering, oxygenating blood and blood components, dialysis, blood purification or clearing, pathogen removal, blood and blood component warming, blood component washing, and red blood cell deglycerolization. The present invention provides improved methods of blood processing wherein a blood sample or component thereof is separated into components or subcomponents on the basis of density, size, diffusion rate, sedimentation velocity, surface chemistry properties or combinations of these characteristics.

"Observation region" refers to an illuminated portion of an object or plurality of objects. At least a portion of transmitted light, scattered light or both from the observation region is collected by a light collection element and detected by a detector. In preferred embodiments of the present invention, the observation region is positioned on a blood-processing device, component of a blood-processing device, such as an optical cell, or a blood sample container. The size and position of the observation region is determined by the field of view of the light collection element, the position of the light collection element from the blood processing device, the area of the detector and the position of the detector with respect to the light collection element. In an embodiment, the size, shape and position of the observation region is selectively adjustable by controlling the position of the light collection element with respect to the blood processing device and the field of view of the light collection element. In an embodiment of the present invention, one or more phase boundaries between optically differentiable components are viewable in the observation region. In another preferred embodiment, at least one separated component is viewable in the observation region. In another preferred embodiment, at least one extraction port is viewable in the observation region.

"Blood sample" and "blood" are used synonymously to refer to whole blood, one or more blood component, one or more blood products, or any combination of these. "Blood component" and "blood product" as used herein include cellular components, non-cellular components of blood and combinations of cellular and non-cellular components of blood. Exemplary cellular components include but are not limited to erythrocytes (red blood cells), leukocytes (white blood cells), and thromobocytes (platelets) and combinations of these materials. Leukocytes comprise monocytes, granulocytes, agranulocytes, and lymphocytes. Exemplary noncellular components include but are not limited to plasma, dissolved salts and minerals and plasma proteins. A blood component can be further fractionated into blood sub-components.

"Epi-illumination" refers to the illumination of an object and generation of scattered light. In epi-illumination, light is directed to the object along an axis of illumination that is different than the optical axis whereby scattered light is collected and detected.

"Parallel", in a physical, non-electrical sense, refers to a geometry in which two surfaces are equidistant from each other at all points and have the same direction or curvature. Substantially parallel refers to a geometry in which angular deviations from absolute parallelism are less than 10 degrees, and preferably less than 0.5 degrees for some applications.

In the following description, numerous specific details of the devices, device components and methods of the present invention are set forth in order to provide a thorough explanation of the precise nature of the invention. It will be apparent, however, to those of skill in the art that the invention can be practiced without these specific details. Reference in the specification to "a preferred embodiment," "a more preferred embodiment" or "an exemplary embodiment" means that a particular feature, structure, or characteristic set forth or described in connection with the embodiment is included in at least one embodiment of the invention. References to "preferred embodiment," "a more preferred embodiment" or "an exemplary embodiment" in various places in the specification do not necessarily refer to the same embodiment.

FIG. 1 schematically illustrates an exemplary embodiment of the optical monitoring system of the present invention capable of measuring a distribution of scattered and/or transmitted light intensities corresponding to patterns of light originating from an observation region on a separation chamber. The illustrated monitoring system 100 comprises light source 110, light collection element 120, and detector 130. Light source 110 is in optical communication with a density centrifuge 140 comprising separation chamber 150, which rotates about central rotation axis 160. Rotation about central rotation axis 160 results in separation of a blood sample in the separation chamber into discrete blood components along a plurality of rotating separation axes oriented orthogonal to the central rotation axis 160. In a preferred embodiment, separation chamber 150 is held in a circular filler (not shown in FIG. 1), which is also capable of rotation about central rotation axis 160. The filler may comprise a disc having an internal, circular groove wherein the separation chamber is positioned and fastened. During operation of the density centrifuge, the filler is operationally connected to a rotating means such that both filler and separation chamber are rotated about the central rotation axis 160. In the schematic shown in FIG. 1, the blood sample is separated into an outer higher density phase corresponding to a red blood cell component 170, an intermediate density phase corresponding to a white blood cell and platelet-containing component (e.g. buffy coat) 180 and a lower density inner phase corresponding to a platelet enriched plasma component 190.

Light source 110 provides incident light beam 200, which illuminates an observation region 220 on separation chamber 150, preferably in a manner generating scattered and/or transmitted light from the blood sample undergoing separation. In one embodiment, light source 110 is capable of generating an incident light beam, a portion of which is transmitted through at least one blood component undergoing separation in separation chamber 150. At least a portion of scattered and/or transmitted light 210 from the observation region 220 is collected by light collection element 120. Light collection element 120 is capable of directing at least a portion of the collected light 210 onto detector 130. The detector 130 detects patterns of scattered and/or transmitted light 210 from the observation region, thereby measuring distributions of scattered and/or transmitted light intensities. In an exemplary embodiment, distributions of scattered and/or transmitted light intensities comprise images corresponding to patterns of light originating from the observation region 220. In one embodiment, images of the present invention are monochrome images, which provide a measurement of the brightness of separated blood components along the separation axis. Alternatively, images of the present invention are color images, which provide a measurement of the colors of separated blood components along the separation axis.

Observation region 220 is positioned on a portion of the density centrifuge 140, preferably on the separation chamber 150. In the exemplary embodiment illustrated in FIG. 1, separated blood components and phase boundaries between optically differentiable blood components are viewable in observation region 220. In one embodiment, the observation region is positioned on an optical cell of the separation chamber having windows for transmitting the incident beam through the blood sample undergoing processing. In an alternative preferred embodiment, one or more extraction ports (not shown in FIG. 1) are viewable in observation region 220. In another embodiment, observation region 220 is positioned on the top of the separation chamber 150 such that leaks of the blood sample and/or improper alignment of the separation chamber or filler are viewable. In another alternative embodiment, the observation region 220 is positioned on a portion of the separation chamber such that the composition of a separated blood component can be directly monitored. For example, a monitoring system of the present invention provides a method of characterizing the type of cellular component collected and counting the amount of cells extracted from the separation chamber as a function of time. Alternatively, the monitoring system is arranged such that the concentration of non-cellular blood components, such as blood plasma proteins, is directly measured. In one embodiment, the observation region 220 is arranged such that a plurality of measurements are obtained from every measured distribution of scattered and/or transmitted light intensities.

Optionally, the observation region 220 can also be illuminated by epi-illumination light source 230, which is positioned on the same side of the separation chamber as the light collection element and detector. Epi-illumination light source 230 is positioned such that it generates an incident beam 240, which is scattered by the blood sample and/or centrifuge. A portion of the light from epi-illumination light source 230 scattered by the separation chamber and is collected by light collection element 120 and detected by detector 130, thereby measuring a distribution of scattered and/or transmitted light intensities.

In one embodiment, detector 130 is also capable of generating output signals corresponding to the measured distributions of scattered and/or transmitted light intensities and/or images. In the exemplary embodiment shown in FIG. 1, detector 130 is operationally connected to a centrifugation device controller 225 capable of receiving the output signals. In one embodiment, centrifugation device controller 225 displays the measured intensity distributions, stores the measured intensity distributions, processes measured intensity distributions in real time, transmits control signals to various optical and mechanical components of the monitoring system and centrifuge or any combination of these. In a preferred embodiment, centrifugation device controller 225 is operationally connected to centrifuge 140 and is capable of adjusting selected operating conditions of the density centrifuge, such as the flow rates of cellular and non-cellular components out of the separation chamber, the position of one or more phase boundaries along the separation axes, rotational velocity of the separation chamber about central rotation axis 160, the infusion of anticoagulation agents or other blood processing agents to the blood sample, or any combination of these.

As shown in FIG. 1, centrifugation device controller 225 can also be operationally connected to light source 110 and/or epi-illumination light source 230. In this embodiment, centrifugation device controller 225 and/or detector 130 are capable of generating output signals for controlling illumination conditions. For example, output signals from detector can be used to control the timing of illumination pulses, illumination intensities, the distribution of illumination wavelengths and/or position of light source 110 and/or epi-illumination light source 230. As also shown in the embodiment illustrated in FIG. 1, centrifugation device controller and detector are in two-way communication. In this embodiment, centrifuge device controller sends control signals to detector 130 to selectively adjust detector exposure time, detector gain and to switch between monochrome and color imaging.

Referring again to the embodiment illustrated in FIG. 1, light collection element 120, detector 130, or both, can be arranged such that they are moveable, for example moveable along a first detection axis 250, which is oriented orthogonal to the central rotation axis of the centrifuge. Movement of light collection element 120 in a direction along detection axis 250 adjusts the position of observation region 220 on the density centrifuge. In another embodiment, light collection element 120 is also capable of movement in a direction along a second detection axis (not shown), which is orthogonal to the first detection axis 250. The present invention also includes an embodiment wherein light source 110, epi-illumination light source 230, or both, are also capable of movement in a manner to optimize illumination and subsequent detection of transmitted and/or scattered light from the selectively adjustable observation region.

Light sources of the present invention comprise light emitting diode sources capable of generating one or more incident beams for illuminating an observation region on the density centrifuge. A plurality of lamps may be positioned to illuminate a single side or multiple sides of a density centrifuge. Light sources useable in the present invention include light emitting diodes and arrays of light emitting diode light sources. Use of light emitting diode light sources is preferred for some applications because they are capable of generating precisely timed illumination pulses. Preferred light sources generate an incident light beam having a substantially uniform intensity. In one embodiment, light sources of the present invention generate an incident beam having a selected wavelength range and selected intensity.

In a preferred embodiment, the optical monitoring system of the present invention comprises a plurality of light sources, each capable of generating an incident light beam having a different wavelength range. In one embodiment, for example, the optical monitoring system of the present invention comprises a combination of any of the following: white light source, red light source, green light source, blue light source and infra red light source. Use of a combination of light sources having different wavelength ranges is beneficial for discriminating and characterizing separated blood fractions because absorption constants and scattering coefficients of cellular and non-cellular components of blood vary with wavelength. For example, a red blood cell containing component is easily distinguished from platelet enriched plasma containing component by illumination with light having wavelengths selected over the range of about 500 nm to about 600 nm because the red blood cell component absorbs light over this wavelength significantly more strongly that the platelet enriched plasma containing component. In addition, use of multiple colored light sources for illumination provides a means of characterizing the white blood cell type in an extracted blood component. As different white blood cell types have different absorption and scattering cross sections at different wavelengths, monitoring transmitted and/or scattered light from a white cell-containing blood component provides a means of distinguishing the various white blood cell types in a blood component and quantifying the abundance of each cell-type.

Light sources of the present invention provide a continuous incident light beam or a pulsed incident light beam. Pulsed light sources are capable of being switched on and off in a manner synchronous with the rotation of the separation chamber to provide distributions of transmitted and/or scattered light intensities corresponding to an observation region having a substantially fixed position using sensors, switches or other types of known cooperation. Alternatively, pulsed light sources of the present invention can be configured such that they can be switched on and off in a manner asynchronous with the rotation of the separation chamber providing distributions of transmitted and/or scattered light intensities corresponding to different observation regions for each full rotation. This alternative embodiment provides a method of selectively adjusting the location of the observation region and, thereby, probing different regions of the separation chamber. In one embodiment, triggering of illumination pulses is based on the rotational speed of the centrifuge or can be based on the angular position of the separation chamber as detected by optical or electronic methods well known in the art. In a preferred embodiment, triggering is provided by trigger pulses generated by the centrifuge device controller and/or detector.

An illumination system of the present invention also includes one or more aperture plates capable of providing a selected illumination area on a blood processing device or component thereof. In a preferred embodiment, an aperture plate is positioned between the light source and the blood sample undergoing separation. In this embodiment, the aperture plate masks areas of the separation chamber where exposure to light causes unwanted scattered light. In some instances, the reduction of unwanted scattered light detected by the detector reduces noise and, therefore, improves signal-to-noise ratio and image quality. Aperture plates are typically integrated into a filler that holds the separation chamber in place during rotation. In this embodiment, the aperture plate rotates with the separation chamber. Optical filters and polarizers can also be incorporated into the illumination system of the present invention to provide illumination beams having selected optical properties, such as intensity, power, wavelength range and polarization state. Diffusers can also be incorporated into the illumination system of the present invention to provide spatially uniform illumination beams as is well known in the art.

Figure 2:
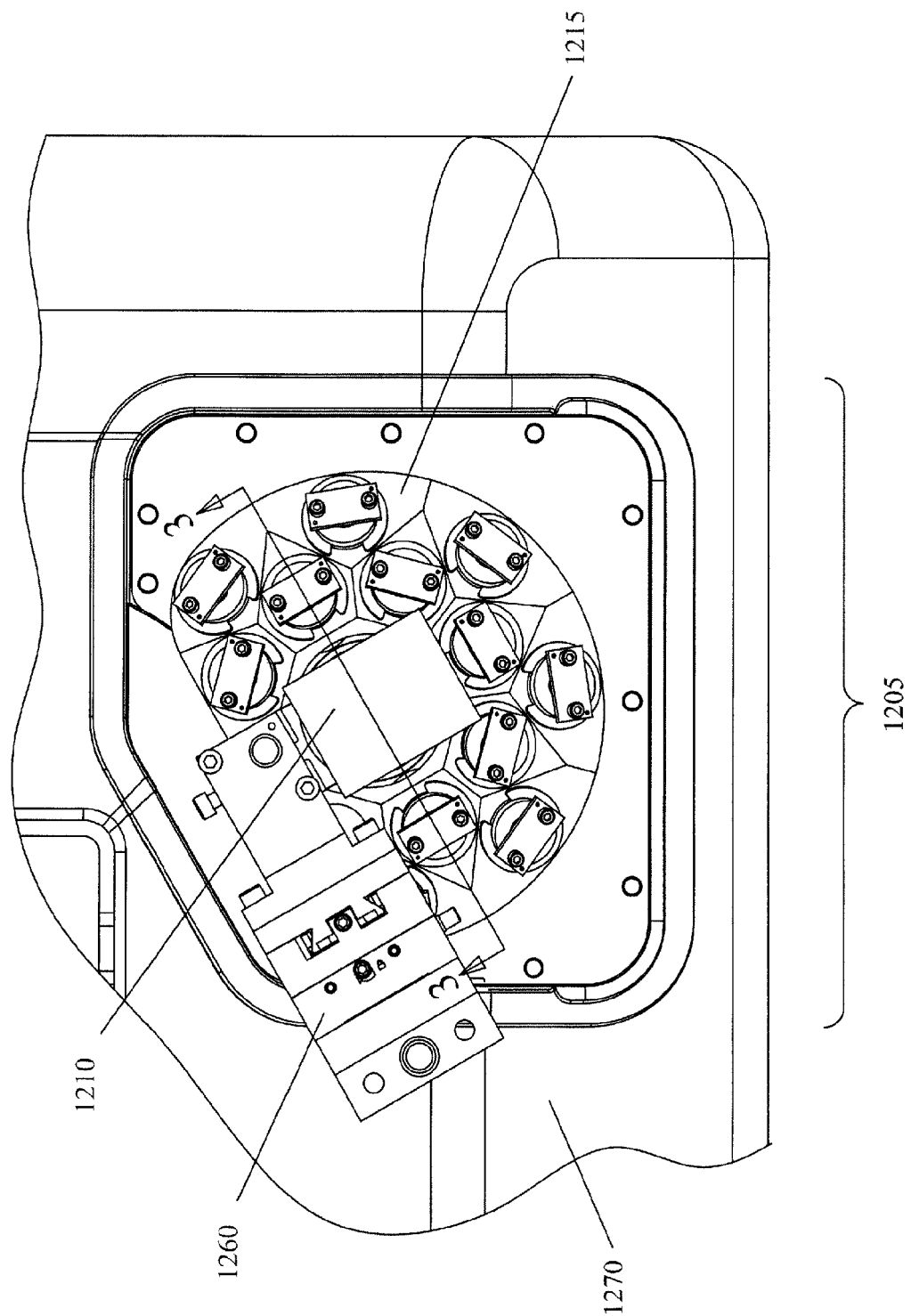
FIG. 2 is a top view of an optical monitoring and control system of the present invention well suited for blood processing via density centrifugation.

The optical monitoring and control system comprises a light source, a close-focus lens system and a digital camera, arranged as illustrated in FIGS. 1 and 2. Illumination is provided by a light source positioned beneath the separation chamber. The light source is capable of directing light through a white blood cell extraction port of the optical cell. Illumination is also provided to the top of the optical cell. Light transmitted through and scattered by the optical cell is collected by the close focus lens system and detected by the digital camera. Distributions of transmitted and scattered light are acquired for every other rotation of the separation chamber.

Measurements generated from the operation of image-data analysis algorithms and process control algorithms may also serve as the basis of output signals sent to the camera and light collection element 120, and light source and camera triggering hardware 110, 230 to optimize the quality of the images acquired and analyzed. For example, output signals can adjust in the intensity of the illumination beam, change the color of the illumination beam, or adjust the camera's gain or exposure time.

The present invention includes systems for monitoring and controlling blood processing via density centrifugation that are capable of providing simultaneous real time measurements of the positions of phase boundaries between optically differentiable blood components relative to calibration markers and the compositions and/or fluxes of separated and extracted blood components. A system of the present invention exhibiting excellent sensitivity, mechanical ruggedness and reliability comprises a fixed position CCD camera equipped with a fixed focus lens, a top pulsed LED (light emitting diode) light source and a bottom pulsed LED light source. Use of a fixed position CCD camera equipped with a fixed focus lens system provides a system exhibiting high mechanical stability with respect to maintaining optical alignment, which avoids the need for periodic adjustments of the optical path lengths illumination and detection beams. In addition, use of top and bottom pulsed LED light sources provides considerable flexibility in the wavelength distributions and intensities of illumination light beams directed onto the blood processing system and subsequently detected. Further, use of top and bottom pulsed LED light sources also provides accurate and reproducible temporal characteristics of illumination pulses useful for generating high optical quality images of a rotating optical cell of a separation chamber.

Figure 3:
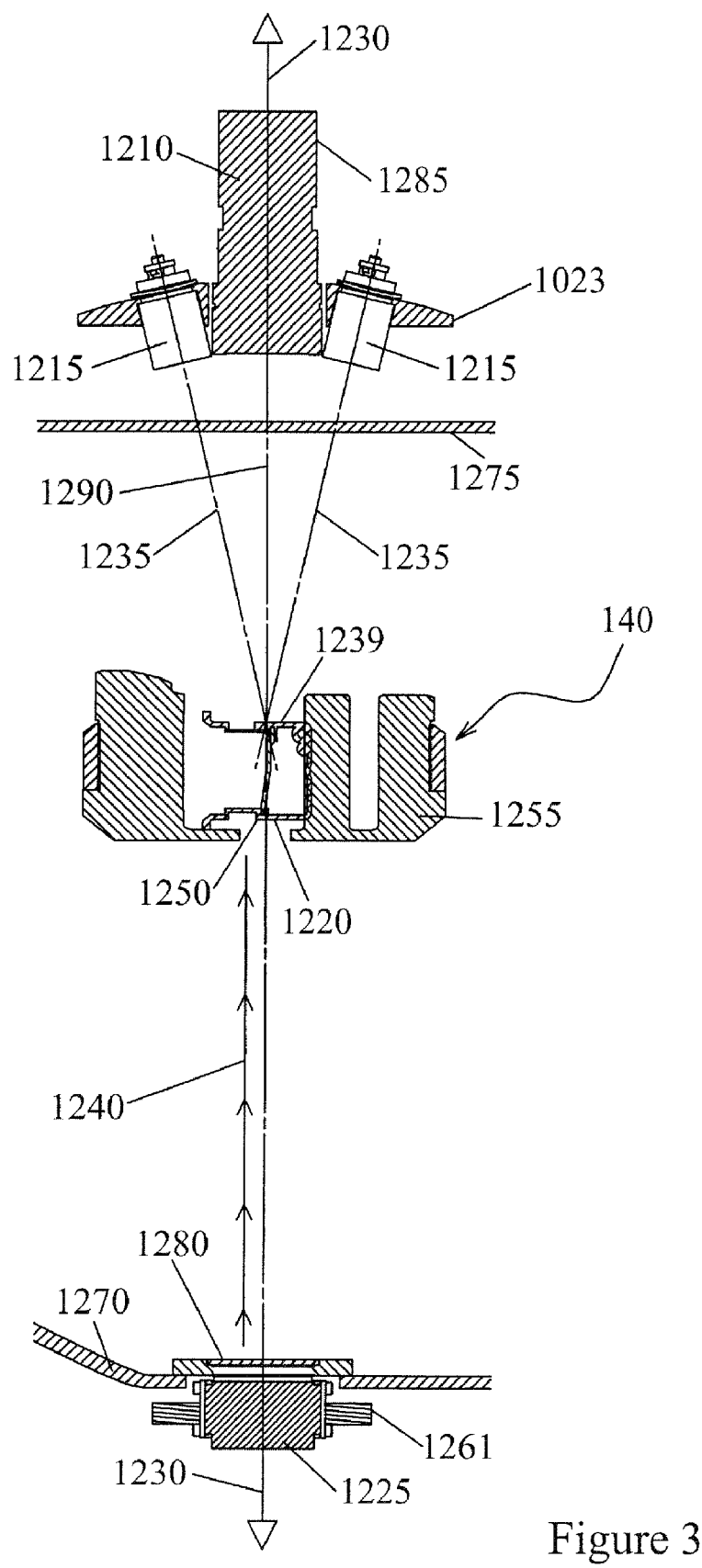
FIG. 3 is a cut away view corresponding to cut away line 3-3 indicated in FIG. 2.

FIG. 2 is a top view of an optical monitoring and control system of the present invention well suited for blood processing via density centrifugation. FIG. 3 is a cut away view corresponding to cut away line 3-3 indicated in FIG. 2. FIG.

4 is a perspective side view of the optical monitoring and control system illustrated in FIGS. 2 and 3. The illustrated optical monitoring and control system 1205 comprises CCD camera equipped with a fixed focus lens system 1210, an optical cell 1220, a top pulsed LED light source 1215, and a bottom pulsed LED light source 1225. As illustrated in FIG. 3, CCD camera with a fixed focus lens system 1210 is in optical communication with optical cell 1220 and positioned to intersect optical axis 1230. Top pulsed LED light source 1215 is in optical communication with optical cell 1220 and is positioned such that it is capable of directing a plurality of collimated upper illumination light beams 1235, propagating along propagation axes that intersect optical axis 1230, onto the top side 1239 of optical cell 1220. Bottom pulsed LED light source 1225 is also in optical communication with optical cell 1220 and is positioned such that it is capable of directing a plurality of collimated bottom illumination light beams 1240, propagating along a propagation axis parallel to optical axis 1230, onto the bottom side 1250 of optical cell 1220.

In an exemplary embodiment, top pulsed LED light source 1215 is positioned about 4.26 inches from the top 1239 of optical cell 1220, and bottom pulsed LED light source 1225 is positioned about 7.47 inches from the top 1239 of optical cell 1220. In the exemplary embodiment shown in FIG. 3, CCD camera with fixed focus lens system 1210 is positioned such that the focal plane of fixed focus lens system is substantially co-planar with selected optical surfaces of optical cell 1220, such as optical surfaces corresponding to an interface monitoring region, calibration markers, one or more extraction ports and one or more inlets. In this embodiment, the CCD camera is also separated from the center of the fixed focus lens system by a distance along optical axis 1230 such that an image corresponding to selected optical surfaces of optical cell 1220 is provided on the sensing surface of the CCD camera. An advantage of this optical configuration is that it allows distributions of light intensities comprising images of top 1239 of rotating optical cell 1220 to be measured and analyzed in real time.

Mounting assembly 1260 holds CCD camera with fixed focus lens system 1210 in a fixed position a selected distance along optical axis 1230 from top 1239 of optical cell 1220. The mounting assembly 1260, shown in FIGS. 2-4, comprises a bracket capable of maintaining a fixed position and orientation of CCD camera with fixed focus lens system 1210. Mounting assembly 1260 can also comprise a two-axis locking translation stage, optionally with a two-axis titling mechanism, capable of selectively adjusting the relative orientation and position of the camera and fixed focus lens system with respect to optical cell 1220.

Figure 4:
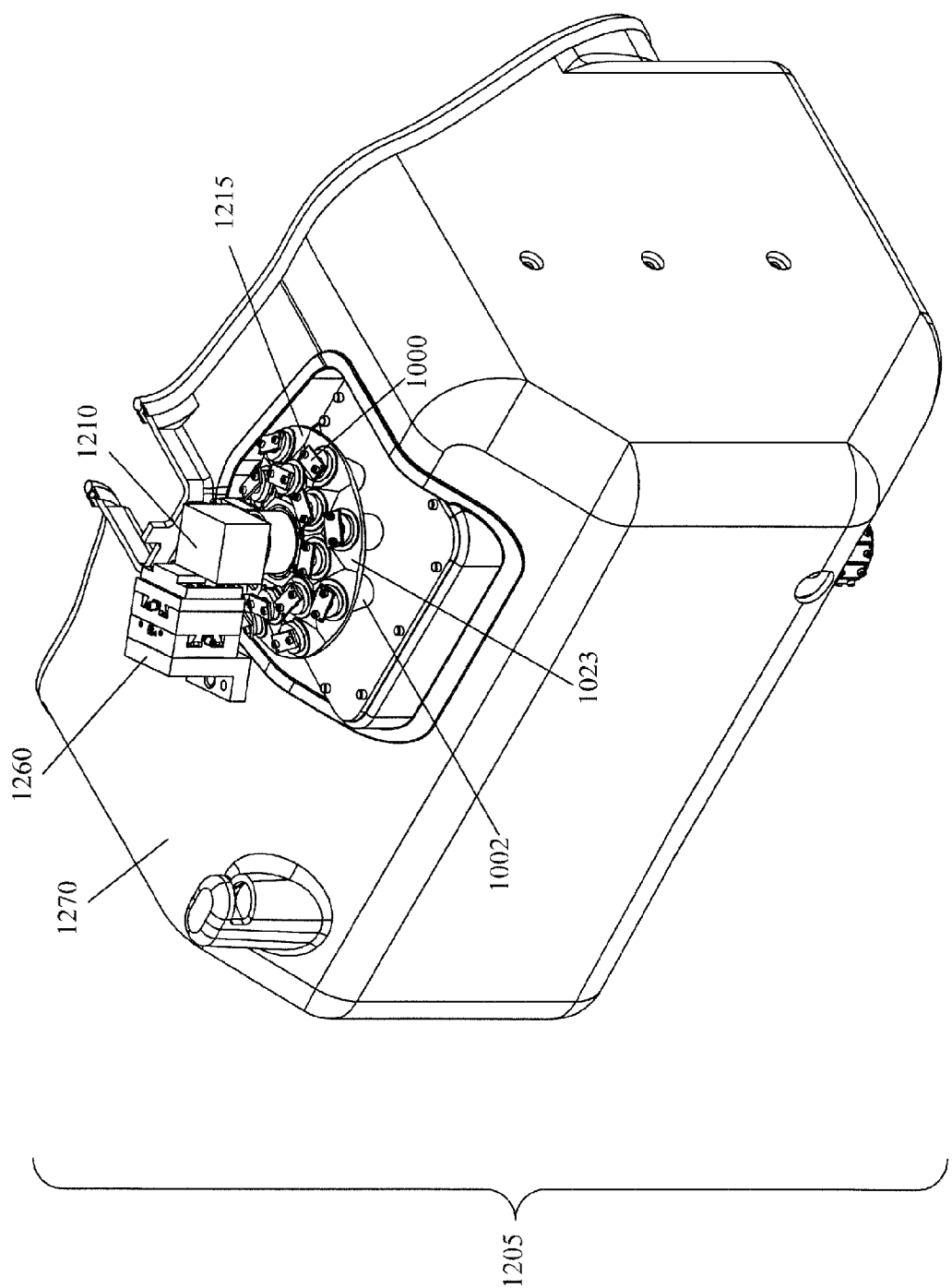
FIG. 4 is a perspective side view of the optical monitoring and control system illustrated in FIGS. 2 and 3.

As shown in FIGS. 2-4, optical monitoring and control system 1205 is integrated directly into a density centrifuge blood-processing device 1265. To provide good mechanical stability of optical monitoring and control system 1205, mounting assembly 1260 is directly affixed to a frame member (not shown in FIGS. 2-4) supporting housing 1270 of density centrifuge blood processing device 1265. In one embodiment, bottom pulsed LED light source 1225 is also affixed to a frame member (not shown in FIGS. 2-4) supporting housing 1270 of density centrifuge blood processing device 1265 by means of an additional mounting assembly 1261. Top pulsed LED light source 1215 is secured to CCD camera with fixed focus lens system 1210, as shown in FIGS. 2-4. Alternatively, top pulsed LED light source 1215 can be directly affixed to a frame member (not shown in FIGS. 2-4) supporting housing 1270 of density centrifuge blood processing device 1265 by means of an additional mounting assembly. Mounting assemblies useful in the present invention comprise any fastening means know in the art, such as clamps, brackets, connectors, couplers, additional housing elements and all known equivalents, and can be affixed to frame members supporting housing 1270 by any means known in the art including the use of bolts, fasteners, clamps, screws, rivets, seals, joints, couplers or any equivalents of these known in the art.

Referring to the cross section shown in FIG. 3, first transparent plate 1275 is provided between CCD camera with a fixed focus lens system 1210 and optical cell 1220, and second transparent plate 1280 is provided between bottom pulsed LED light source 1225 and optical cell 1220. First and second transparent plates 1275 and 1280 physically isolate CCD camera with a fixed focus lens system 1210, top pulsed LED light source 1215 and bottom pulsed LED light source 1225 from optical cell 1220 so that these components will not contact a sample undergoing processing in the event of sample leakage from the separation chamber. In addition, first and second transparent plates 1275 and 1280 minimize degradation of CCD camera with a fixed focus lens system 1210, top pulsed LED light source 1215 and bottom pulsed LED light source 1225 due to unwanted deposition of dust and other contaminants that can be introduced to the system upon rotation of the separation chamber and filler. Further, first and second transparent plates 1275 and 1280 also allow a user to optimize the alignment of the camera with fixed focus lens system, top pulsed LED light source and bottom pulsed LED light source without exposure to a blood sample in the separation chamber. First and second transparent plates 1275 and 1280 can comprise any material capable of transmitting at least a portion of upper and bottom illumination light beams 1235 and 1240. Exemplary materials for first and second transparent plates 1275 and 1280 include, but are not limited to, glasses such as optical quality scratch resistant glass, transparent polymeric materials such as transparent plastics, quartz and inorganic salts.

Figure 5:
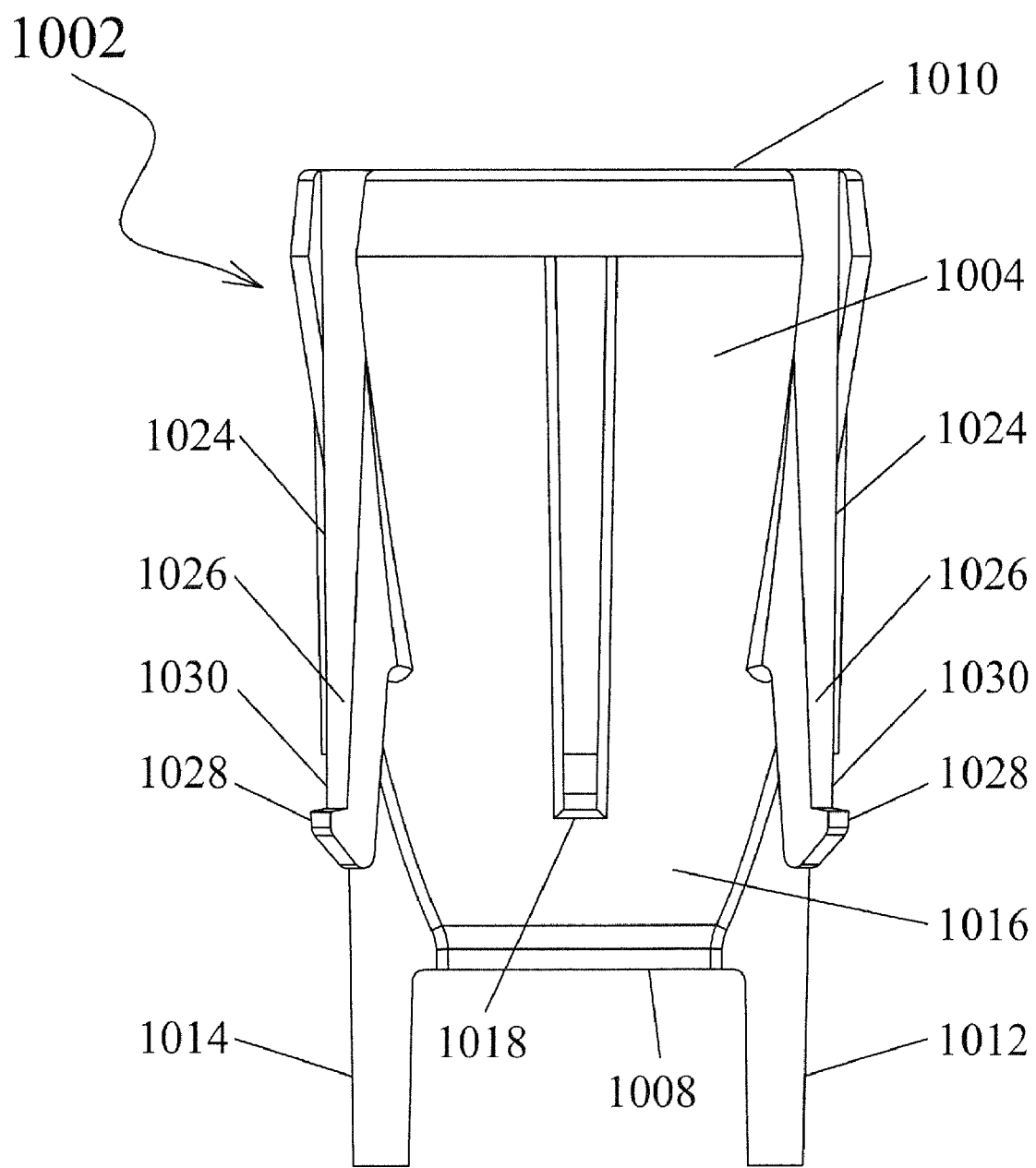
FIG. 5 is a side plan view of a parabolic reflector for use in the optical monitoring and control system.
Figure 6:
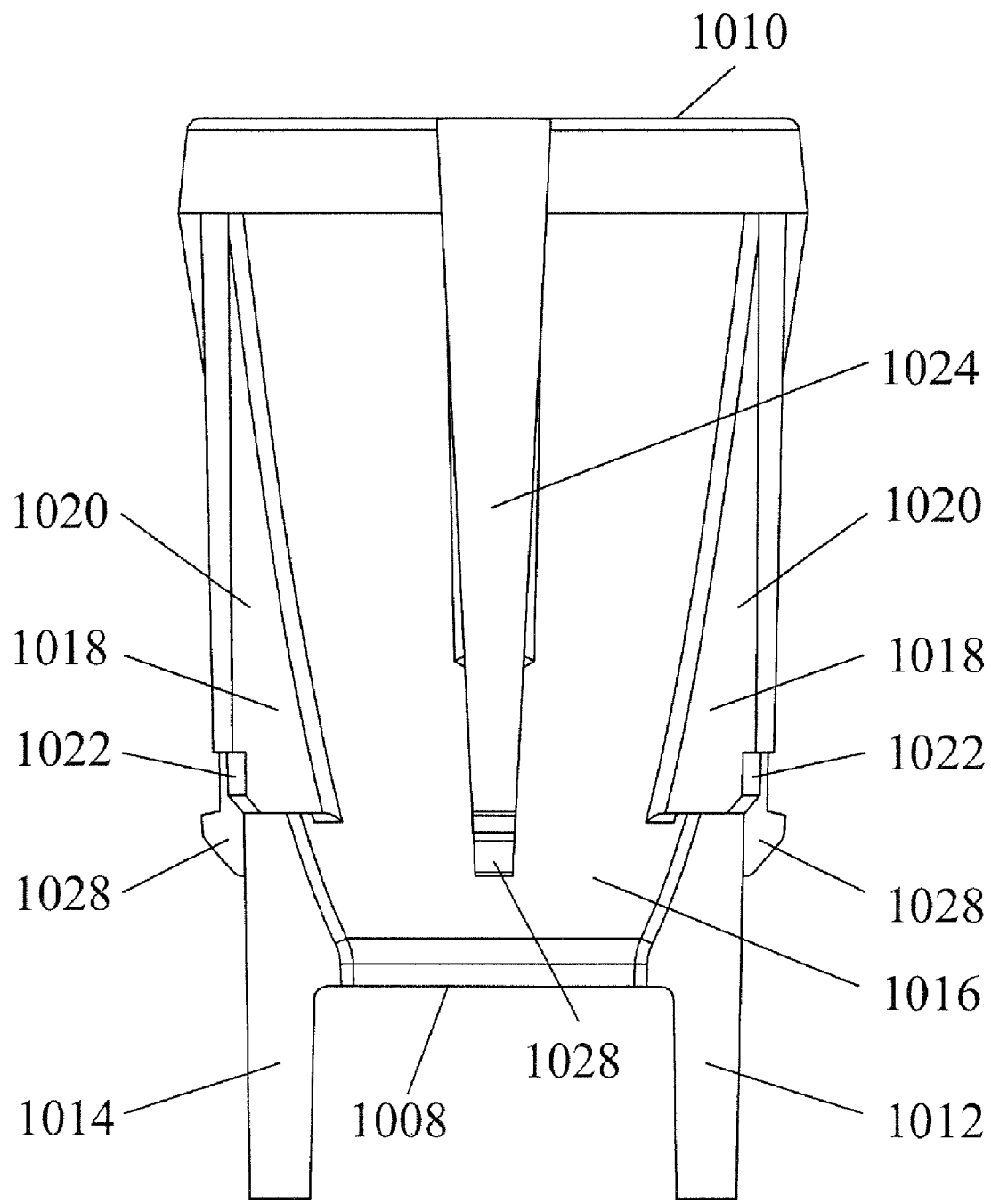
FIG. 6 is another side plan view of the parabolic reflector of FIG. 5, rotated 60 degrees.
Figure 7:
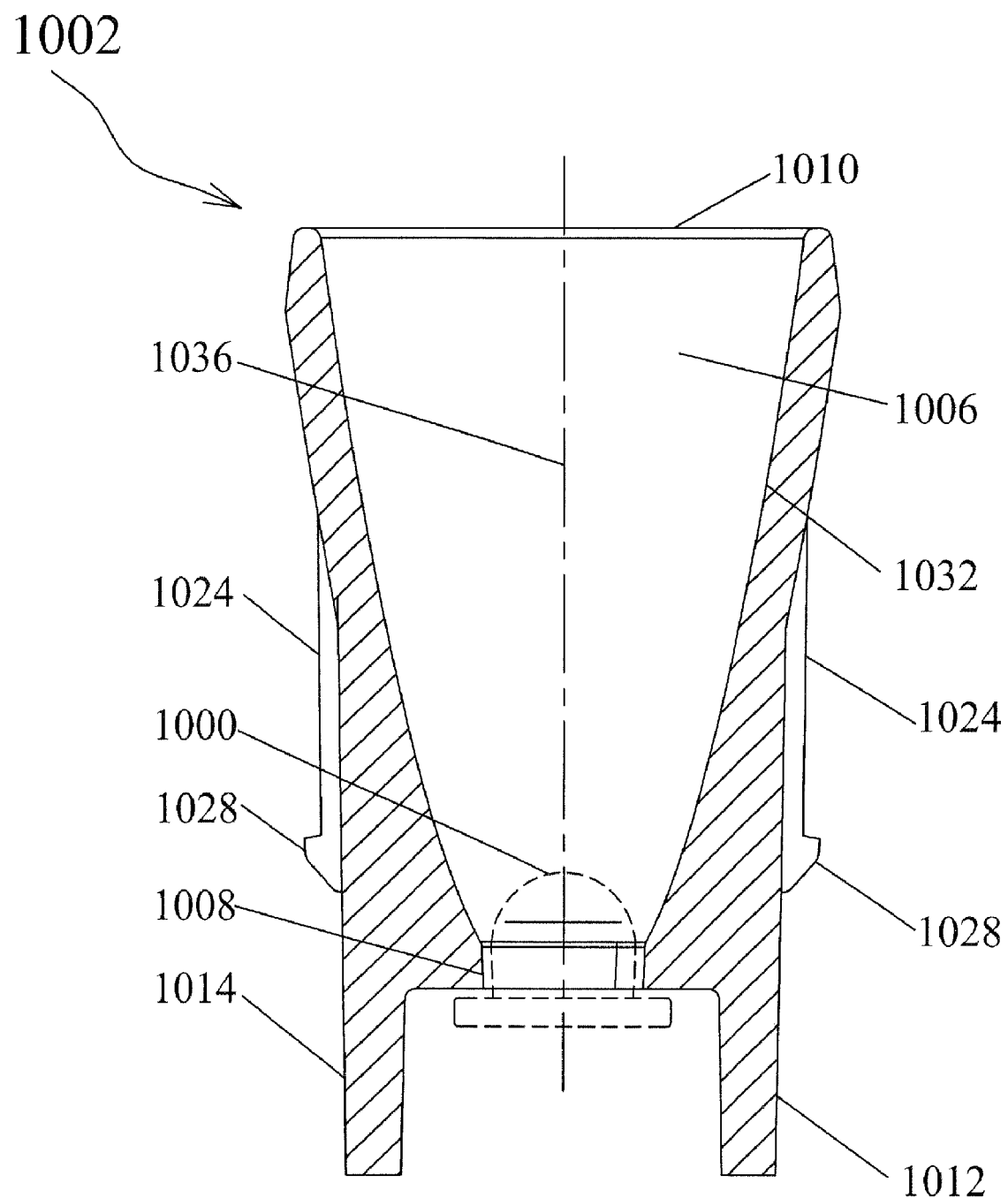
FIG. 7 is a cross sectional view of the parabolic reflector of FIG. 6.

Top pulsed LED light source 1215 and bottom pulsed LED light source 1225 in the optical monitoring and control system illustrated in FIGS. 2-4 each comprise a plurality of LEDs, such as a LED array light source. Top pulsed LED light source 1215 comprises twelve LEDs 1000, each equipped with a parabolic reflector 1002 to provide beam collimation. An exemplary parabolic reflector 1002 is shown in FIGS. 5, 6, and 7. The reflector 1002 comprises a generally frustro-conical body 1004 surrounding a cavity 1006, the cavity having a proximal opening 1008 for receiving an LED device 1000 (shown in dashed lines in FIG. 7) and a distal mouth 1010. A pair of proximally extending fins 1012, 1014 on an outer surface 1016 of the reflector engage the LED 1000. Three longitudinally extending struts 1018 are spaced radially symmetrically around the outer surface 1016 of the reflector. The struts comprise a right triangle 1020 with a right angle apex cut away to form a notch 1022. The struts fit into holes (not shown) in a plate 1023 (see FIG. 4) that supports the twelve LEDs 1000, the notches 1022 resting on the plate. Equidistant between the struts 1018 are three longitudinally extending latches 1024, which are attached radially symmetrically on the outer surface 1016 of the reflector. Each latch comprises a proximally extending arm 1026 with a barb 1028 at a free end 1030 of the arm. The free end 1030 of the arms 1026 snap into holes (not shown) in the plate 1023. After the reflector 1002 is snapped into place in the plate, the LED device 1000 can be inserted into the proximal opening 1008. Light from the LED is reflected from a parabolic mirrored surface 1032 in the cavity 1006. As is known, LED devices emit light from a plate, usually rectangular, and not from a single point that could be made the focal point of a mathematically exact parabolic surface of rotation. Considering the mirrored surface as if it were divided into very thin radial segments, the mirrored surface 1032 is displaced radially outwardly from the location of such a mathematical surface of rotation, causing the focal point of any radial segment of the mirrored surface 1032 to be displaced radially outward from the center of the LED 1002. The focal points form a focal region or a circle with a radius about half the distance from the center of the light emitting plate of the LED to the edge of the plate, thus maximizing the light concentrated by the reflector. The outward displacement of the focal points of the mirrored surface near the LED device 1000 increases the concentration of collected light in the observation region.

Figure 8:
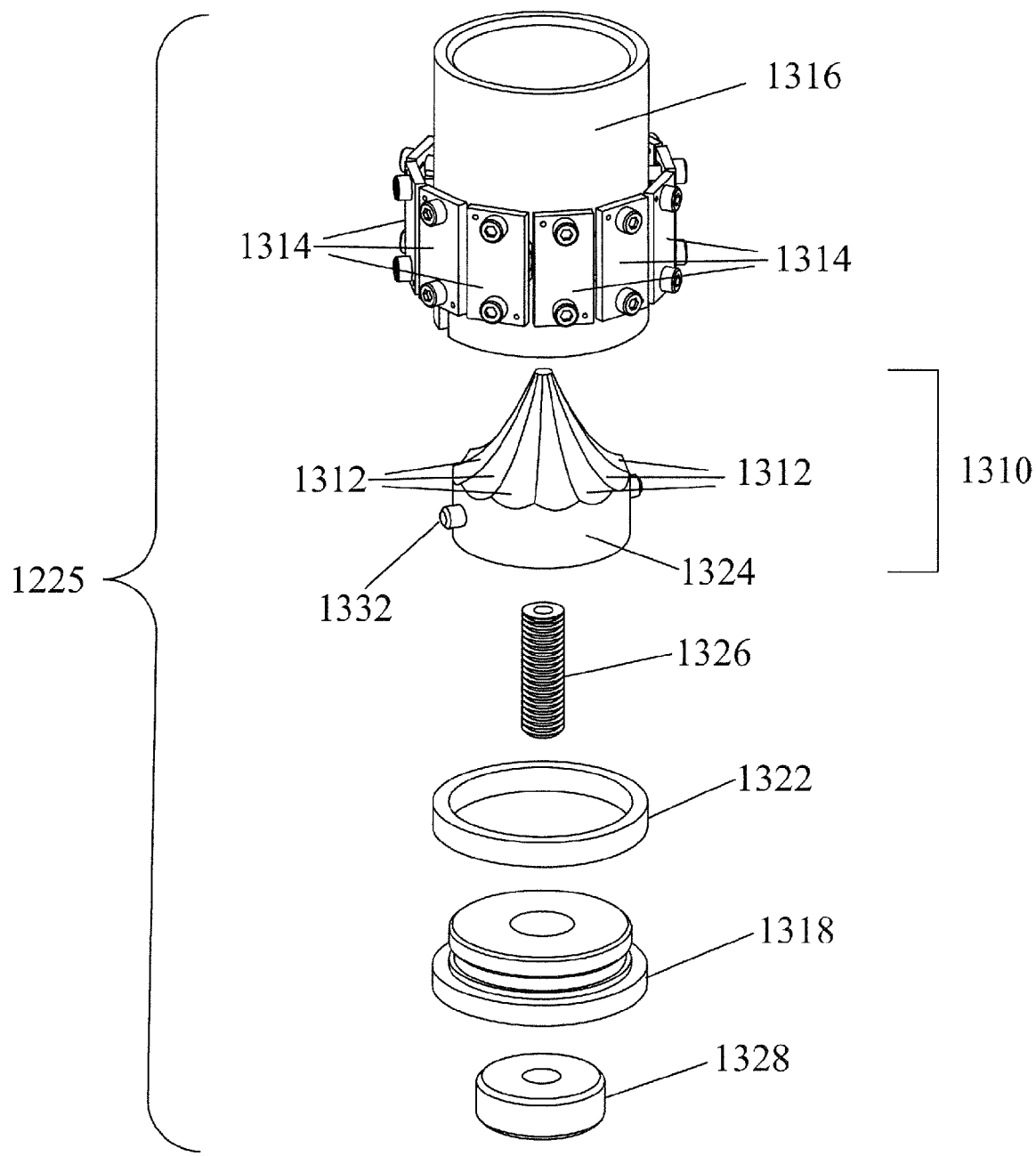
FIG. 8 provides a schematic diagram of an exploded, side view of a bottom pulsed LED light source.

Bottom pulsed LED light source 1225 also comprises twelve LEDs and a collimating optical element, such as one or more lenses, parabolic reflectors or a combination of these elements. FIG. 8 provides a schematic diagram of an exploded, side view of a bottom pulsed LED source 1225 useful in the methods and devices of the present invention. The illustrated pulsed LED light source comprises a collimating optical element 1310 in optical communication with elements 1314 of an LED array. As shown in FIG. 8, collimating optical element 1310 is a multifaceted parabolic reflecting and collimating element comprising a plurality of contoured reflective surfaces 1312, each of which is positioned in optical communication with a LED light element 1314. Contoured reflective surfaces 1312 have a modified parabolic contour profile in one embodiment of the present invention useful for monitoring and controlling blood processing. Depending on the contour profile selected for contoured reflective surfaces 1312, collimating optical element 1310 may be configured to provide a plurality of incident beam propagating along propagation axes that are approximately parallel or a plurality of incident beam propagating along propagation axes which are not parallel. The embodiment illustrated in FIG. 8 is useful for generating a plurality of incident beams that may be directed onto the bottom side 1250 surface of the optical cell 1220.

Figure 9:
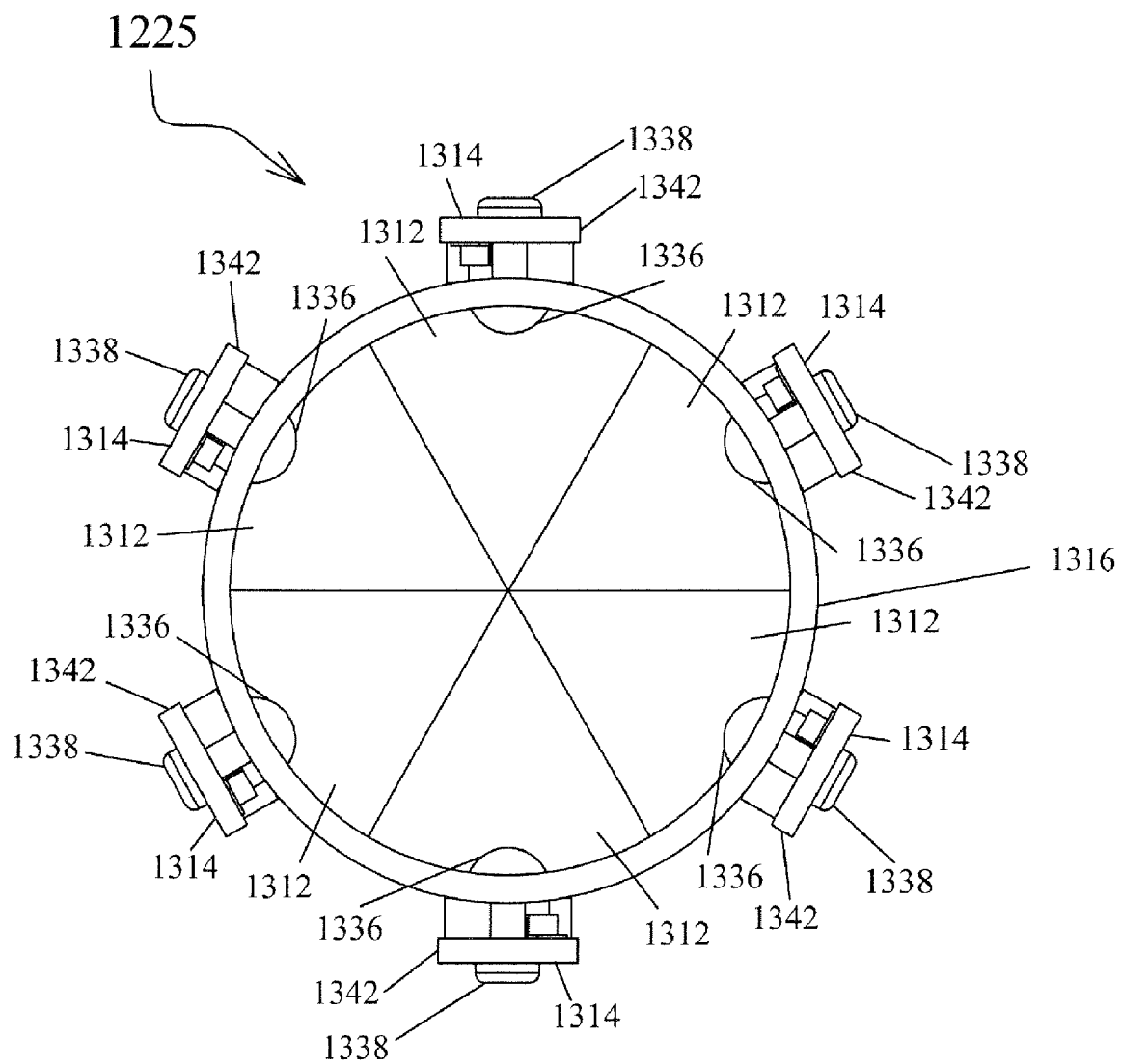
FIG. 9 is a top plan view of a bottom pulsed LED light source having six LED devices.
Figure 10:
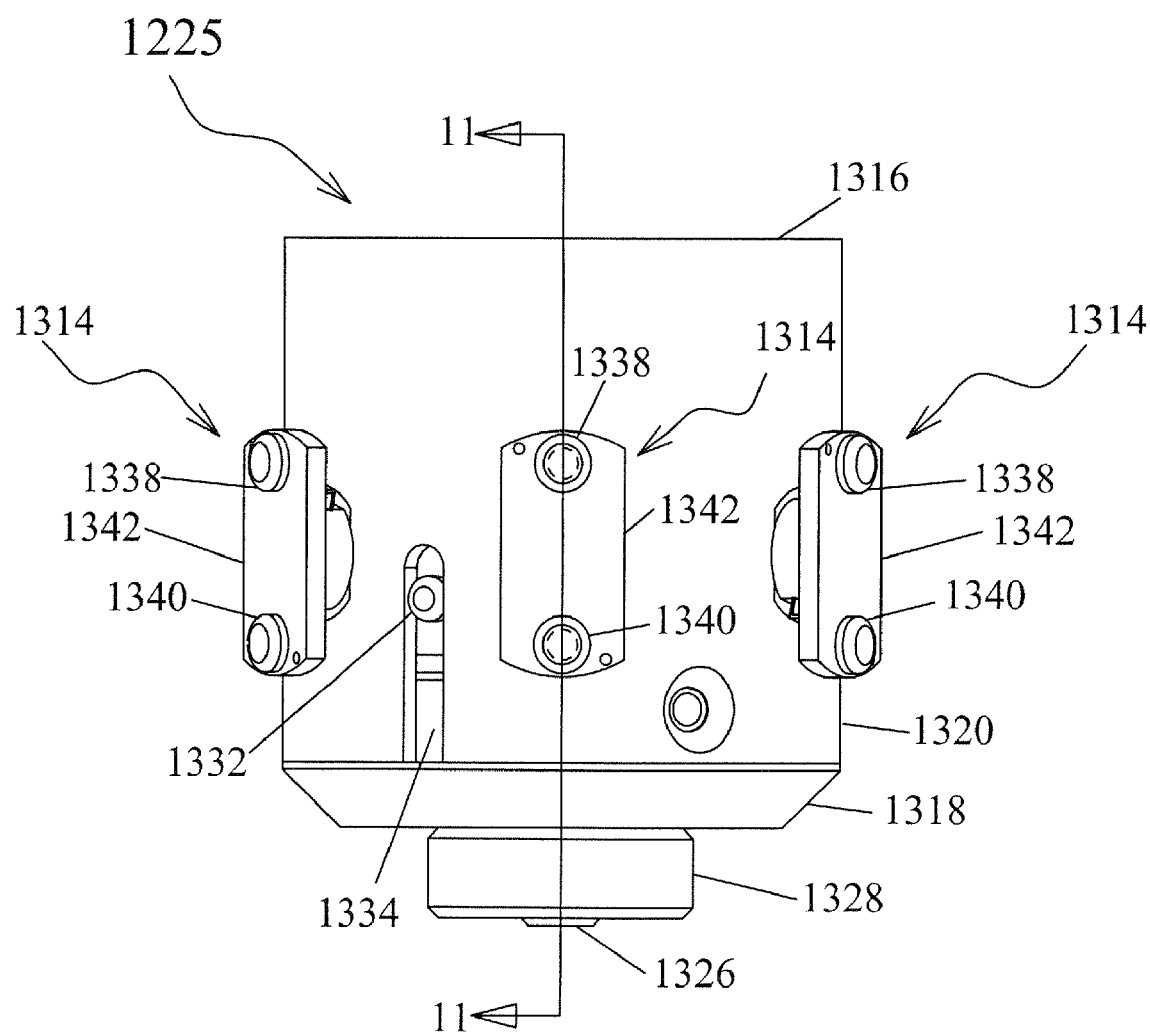
FIG. 10 is a side plan view of the bottom pulsed LED light source of FIG. 9.
Figure 11:
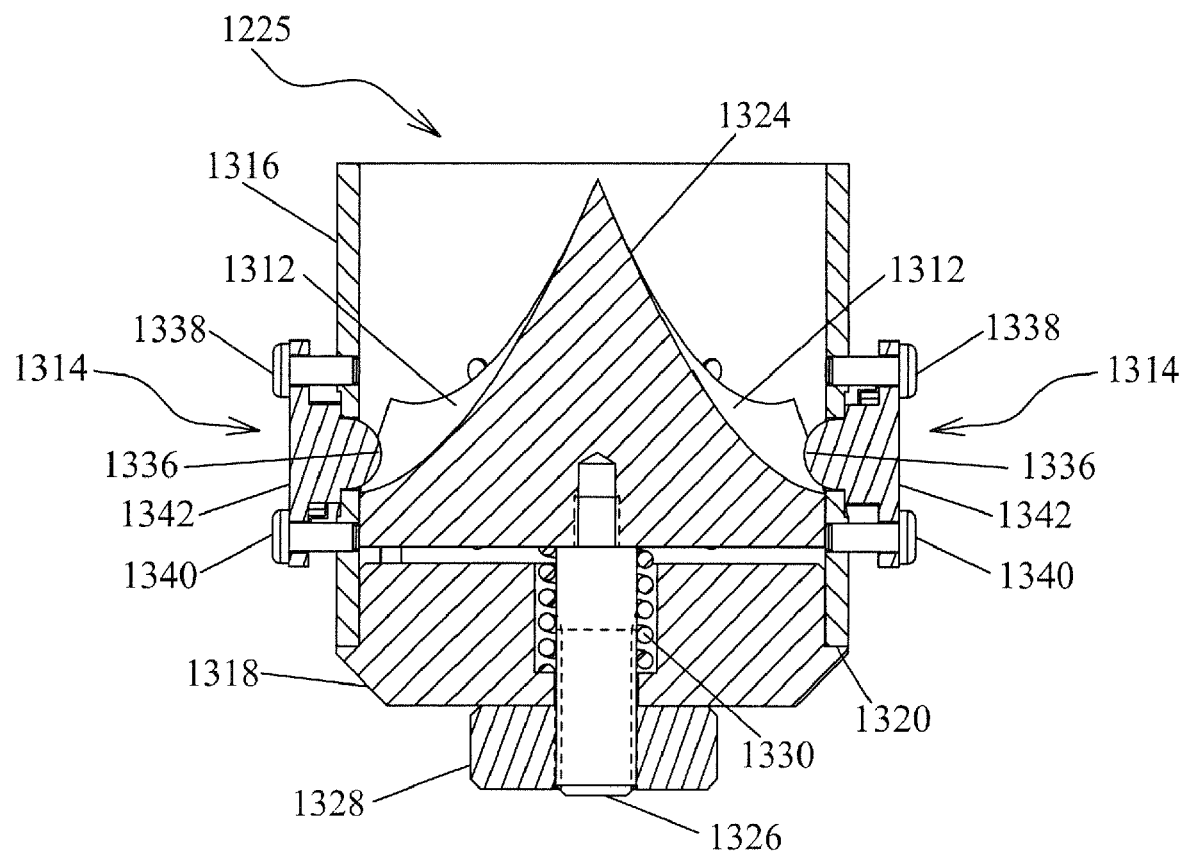
FIG. 11 is a through section of the bottom pulsed light source of FIG. 10 taken along line 11-11 in FIG. 10.

An embodiment of the bottom pulsed LED light source 1225 having six contoured reflective surfaces 1312 is illustrated in FIGS. 9, 10 and 11. The LED light source comprises a cylindrical frame 1316 supporting LED light elements 1314 symmetrically around the outer surface of the frame. A base 1318 may be secured in a proximal end 1320 of the frame 1316 by any suitable means, such as threading, a pressure fit (FIG. 11), a spacer 1322 (FIG. 8), or other means. The contoured reflective surfaces 1312 are formed in a mirror assembly 1324 that is mounted on a threaded shaft 1326. A knob 1328 turns on the threaded shaft 1326 and moves the mirror assembly 1324 up and down within the cylindrical frame 1316 against the resistance of a spring 1330. Pins 1332 on the mirror assembly 1324 slide up and down in slots 1334 in the frame 1316 and prevent the mirror assembly from turning with respect to the frame and the LED light elements 1314. The LED light elements 1314 are mounted in the frame such that light producing parts of an LED device 1336 are in or near the focal region of the adjacent surface 1312. Machine screws 1338, 1340 secure a base 1342 of the LED device to the frame 1316. The bottom light source 1225 can be adjusted, therefore, by adjusting the machine screws to tilt individual LED devices within the frame 1316 and to move the mirror assembly 1324 up and down within the frame.

Figure 12:
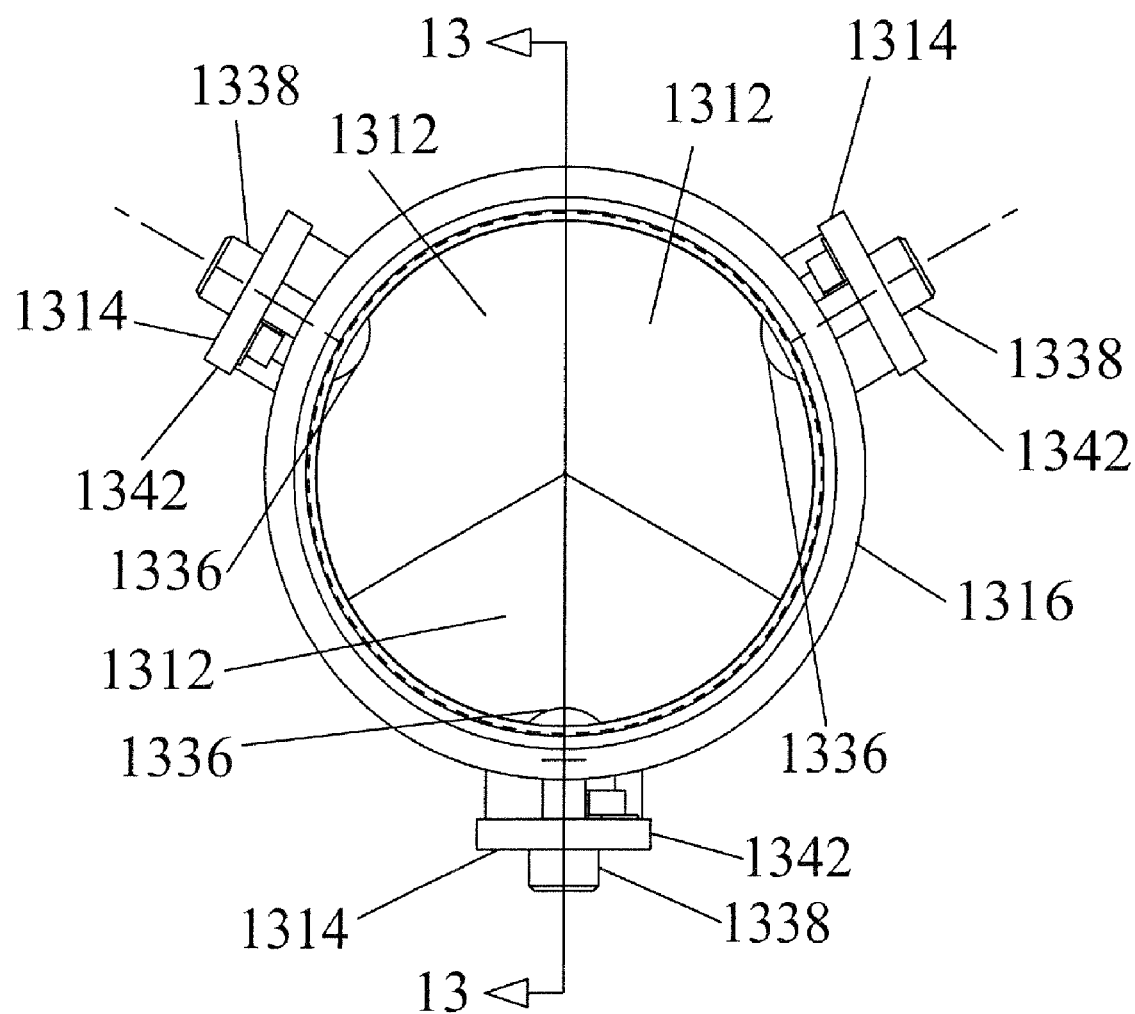
FIG. 12 is a top plan view of a bottom pulsed LED light source having three LED devices.
Figure 13:
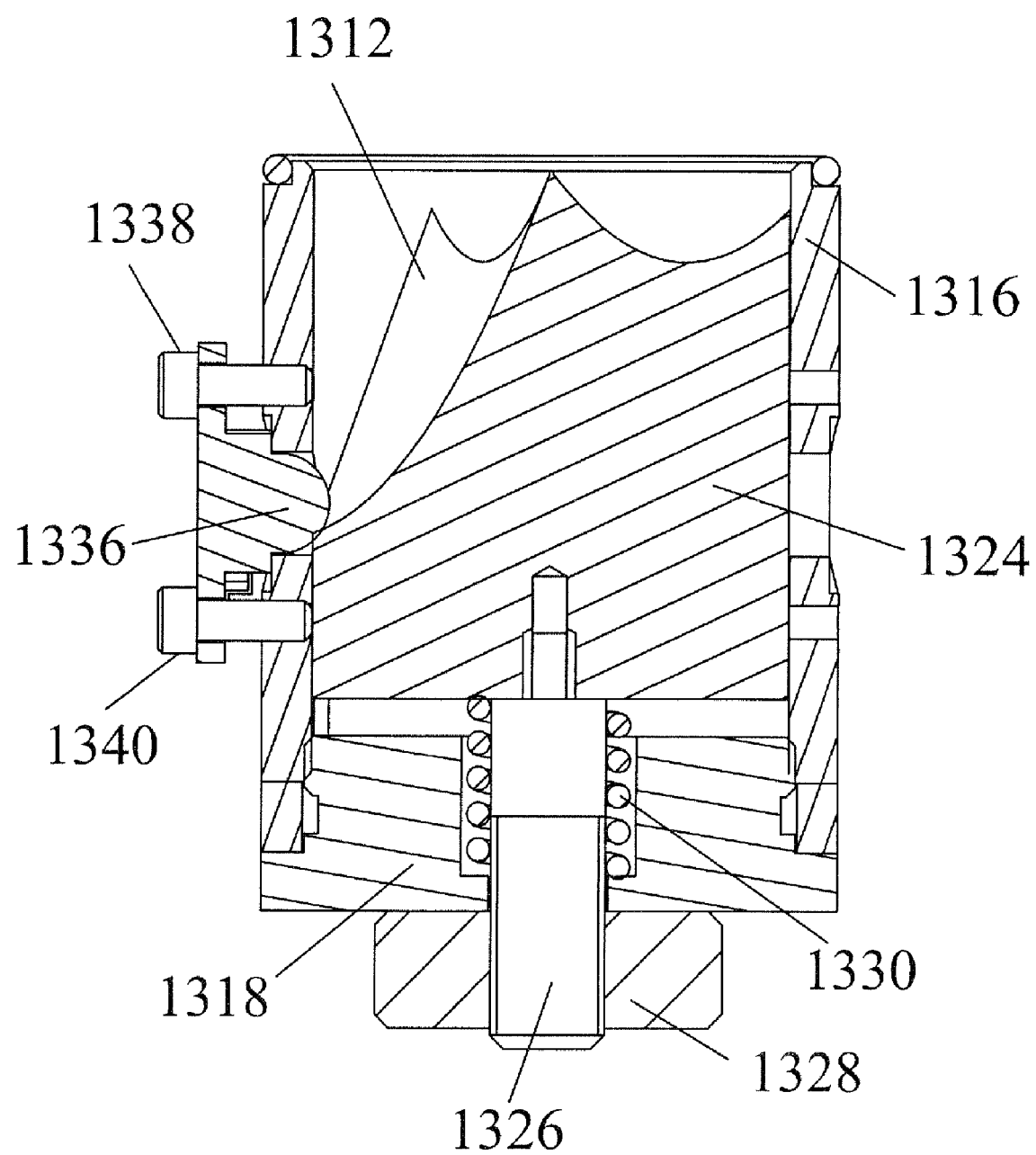
FIG. 13 is a through section of the bottom pulsed LED light source of FIG. 12 taken along line 13-13 in FIG. 12.

The number of LED light elements 1314 and reflective surfaces 1312 may also be reduced to three as shown in FIGS. 12 and 13. The number of LED elements 1314 and reflective surfaces 1312 is selected based on the required illumination and the available power from the LED elements for the particular frequency of emitted light. LED elements vary in the amount of illumination available at a particular frequency. Where greater illumination is needed at a particular frequency, more individual elements 1314 may be needed. At the same time, increased numbers of reflective surfaces 1312 reduces the relative size of those surfaces, thus decreasing the amount of light efficiently reflected into the observation region. In addition, if the capability of selecting different colors using the same bottom array is desired, an array with more (e.g., twelve) LED devices should be selected.

LEDs useful for the top and bottom pulsed LED sources 1215 and 1225 can be red LEDs, green LEDs, white LEDs, infrared LEDs, ultraviolet LEDs or any combination of these. In an exemplary embodiment, top pulsed LED source 1215 comprises two red LEDs, six green LEDs and four white LEDs. LEDs useful in the present invention provide collimated beams having intensities large enough allow measurement of intensity distributions comprising to images of optical cell 1220. In an embodiment of the present invention, LED drive circuitry is optionally positioned proximate to top and/or bottom LED sources to optimize device performance.

Top pulsed LED light source 1215 and bottom pulsed LED light source 1225 are capable of providing synchronized light pulses having accurately selectable temporal characteristics. Pulse widths of light pulses useable in the present invention depend on the rotational velocity of the density centrifuge. Typically, the smaller the pulse width of the light pulse, the less blurring of the optical image corresponding to the acquired distribution of light intensities. However, larger pulse widths allow more photons to be integrated by the CCD of the camera and, thus, provide enhanced signal-to-noise ratios. For a rotational velocity equal to about 3000 RPM, pulse widths less than about 8 microseconds are useful for minimizing blurring of the image of the optical cell generated. Exemplary light pulses useful for some applications of the present invention have pulse widths selected over the range of about 1 microsecond to about 50 microseconds.

In one embodiment, CCD camera with a fixed focus lens system 1210 comprise a monochrome or color CCD camera positioned a fixed, selected distance from a fixed focus lens system. CCD camera and fixed focus lens system can be contained in a housing 1285 capable of maintaining the selected separation distance between these elements and also capable of minimizing detection of unwanted scattered light. Housing 1285 can be equipped with one or more fixed spacers or selectively adjustable spacers for establishing and maintaining a selected distance between the CCD camera and the fixed focus lens system. An exemplary fixed focus lens system comprises a plurality of spherical lenses, cylindrical lenses, spacers or any combination of these elements. An exemplary CCD camera is the "Flea" manufactured by Point Grey Research, Inc. and has a pixel area equal to about 1024 pixels by 768 pixels. An exemplary lens comprises an F 2.8 fixed focal length lens system having a focal length of 28 millimeters manufactured by Schneider Optics, Inc. This combination of exemplary optical components provides a field of view equal to about $3/8$ inch by $1/2$ inch and a depth of field selected over the range of about $1/16$ inch to about $1/2$ inch. This field of view and depth of field allows for measurement of distributions of light intensities comprising images of optical cell 1220 useful for monitoring and controlling the positions of phase boundary positions in an interface region and the compositions of cellular material exiting one or more extraction port. Use of a CCD camera equipped with a fixed focus lens system enhances the mechanical stability of the system and is useful for maintaining selected relative orientations and positions of the CCD camera, fixed focus lens system and the optical cell. This aspect of the present invention provides the system with the ability to make highly reproducible measurements of the positions of phase boundary layers between optically differentiable, separated blood components in an interface region and the compositions of separated blood components exiting the optical cell through one or more extraction ports.

FIG. 3 also shows the optical path lengths provided by the present optical geometry. Top pulsed LED light source 1215 generates a plurality of pulsed collimated upper illumination light beams 1235 which propagate along propagation axes that intersect optical axis 1230. At least a portion of the upper illumination light beams 1235 passes through transparent plate 1275 and is directed onto the top side 1239 of optical cell 1220. A portion of the upper illumination light beams 1235 is scattered by optical cell 1220, one or more separated blood components therein and/or filler 1255. Bottom pulsed LED source 1225 generates a collimated bottom illumination light beams 1240 which propagates along a propagation axis substantially parallel to optical axis 1230. At least a portion of bottom illumination light beams 1240 passes through transparent plate 1280 and is directed onto the bottom side 1250 of optical cell 1220. A portion of bottom illumination light beams 1240 is transmitted through optical cell 1220 and one or more separated blood components therein. Light transmitted through optical cell 1220 can correspond to an interface monitoring region, one or more inlets, one or more extraction ports, one or more calibration markers or any combination of these.

Light 1290 transmitted and/or scattered by optical cell 1220 is collected by fixed focal length lens system and imaged onto the sensing surface of the CCD camera. In this manner, a distribution of light intensities is measured by CCD camera that corresponds to an image of at least a portion of optical cell 1220, such as the top 1239 of optical cell 1220. Detection of scattered light corresponding to the upper illumination light beams 1235 is primarily used for system calibration, proximity identification and translational sensor tracking. Detection of transmitted light corresponding to the bottom illumination light beams 1240 is primarily used for measurement of the position of one or more phase boundary layers of optically differentiable separated blood components in optical cell 1220 and for measurement of the composition and flux of separated blood components exiting one or more extraction ports of optical cell 1220. Detecting transmitted and scattered light arising from both top and bottom illumination maximizes the amount of information that can be extracted from an acquired distribution of light intensities and enhances the multifunctional capabilities of optical monitoring and control systems of the present invention.

Optionally, optical monitoring and control system 1205 may further comprise one or more additional light detectors useful for optimizing the light levels of top and bottom pulsed LED light sources 1215 and 1225. In one embodiment, an additional light detector comprising a photodiode is provided which is capable of measuring scattered light from bottom pulsed LED light source 1225. Use of an additional light detector capable of scattered light from bottom pulsed LED light source 1225 is useful for trouble shooting and error handling aspects of the present invention.

The CCD camera is capable of generating one or more output signals, corresponding to the measured distribution of light intensities. Output signals are sent to one or more centrifuge device controllers, such as a computer or processor, capable of analyzing the acquired distributions of transmitted and/or scattered light intensities and adjusting important operating conditions which affect separation conditions and the composition of extracted blood components. Selectively adjustable operating conditions include, but are not limited to, the rotational velocity of the centrifuge, the flow rates of one or more inlet pumps, and the flow rates of one or more extraction pumps, or any combination of these.

The optical monitoring and control system 1205 is a pulsed optical system, whereby intensity distributions corresponding to optical cell 1220 are acquired as it is rotated about the central rotational axis of the density centrifuge 140. Intensity distributions can be acquired for every full rotation of optical cell 1220 or can be acquired for selected rotations of optical cell 1220, such as every other full rotation. Acquiring intensity distributions for every other rotation of optical cell 1220 is beneficial for some applications because it avoids the need for costly CCD cameras capable of collecting more than about 30 frames per second and also minimizes spatial indication, calibration and optical imaging problems associated with reproducible instrument jitter observed upon rotation of the separation chamber.

To generate intensity distributions corresponding to good images of optical cell 1220, top and bottom illumination pulse, camera shutter and gating settings and the rotation of optical cell 1220 of a separation chamber of a density centrifuge must be accurately synchronized. Accurate synchronization of these elements allows images of transmitted and/or scattered light intensities comprising high optical quality images of the optical cell to be measured for each full rotation or for selected rotations. In the present invention, the rotational position of components of the density centrifuge and/or monitoring and control system, such as the optical cell or separation chamber, is accurately measured using an encoded motor system, as well known in the art. In an exemplary embodiment, density centrifuge 140 is provided with any optical sensor capable of reading a plurality of markers on a rotating element of the density centrifuge. This configuration allows for real time measurements of the rotational position of the optical cell, preferably measurements of rotational position accurate to about 0.09 degrees. This configuration also provides real time measurements of the rotational position of the optical cell when the rotational velocity changes, such as during spin up or spin down of the density centrifuge.

The encoded motor system is also capable of generating output signals in real time corresponding to the rotational position of components of the density centrifuge and/or monitoring and control system, such as the optical cell or separation chamber. In an exemplary embodiment, these output signals are provided as input to a synchronization and timing controller capable of sending one or more trigger signals to the top pulsed LED light source, bottom pulsed LED light source and the CCD camera. Trigger signals provided by the synchronization and timing controller to these device components include the trigger location (i.e. the time or rotational position for initiating to a light pulse), the trigger frequency (i.e. for which rotations should light pulses be generated), the pulse width setting (duration of light pulse) and the delay setting (i.e. time between when the trigger signal is received and when the light pulse is to be initiated). LED elements in top and bottom pulsed LED light sources and camera shutter and gate setting can be accurately triggered at times corresponding to a desired rotational position of the density centrifuge using trigger signals generated by the synchronization and timing controller. Selection of the rotational position corresponding to the trigger signal allows the observation region to be selectively adjusted in the present invention. In this manner, a plurality of selected regions of the optical cell, separation chamber and other components of the density centrifuge are optically probed.

In an exemplary embodiment, the exposure time of the CCD camera is determined by the pulse width of the light pulses generated by the top and bottom pulsed LED light sources, rather than by the gating setting or shutter of the CCD camera. In one embodiment, the shutter of the CCD camera can be opened longer than the light pulse duration without having significant background noise affects. As the pulse widths of light pulses generated by LED light sources can be controlled very accurately, this aspect of the present invention eliminates the need of costly CCD cameras providing very accurate gating corresponding to short exposure times.

Figure 14:
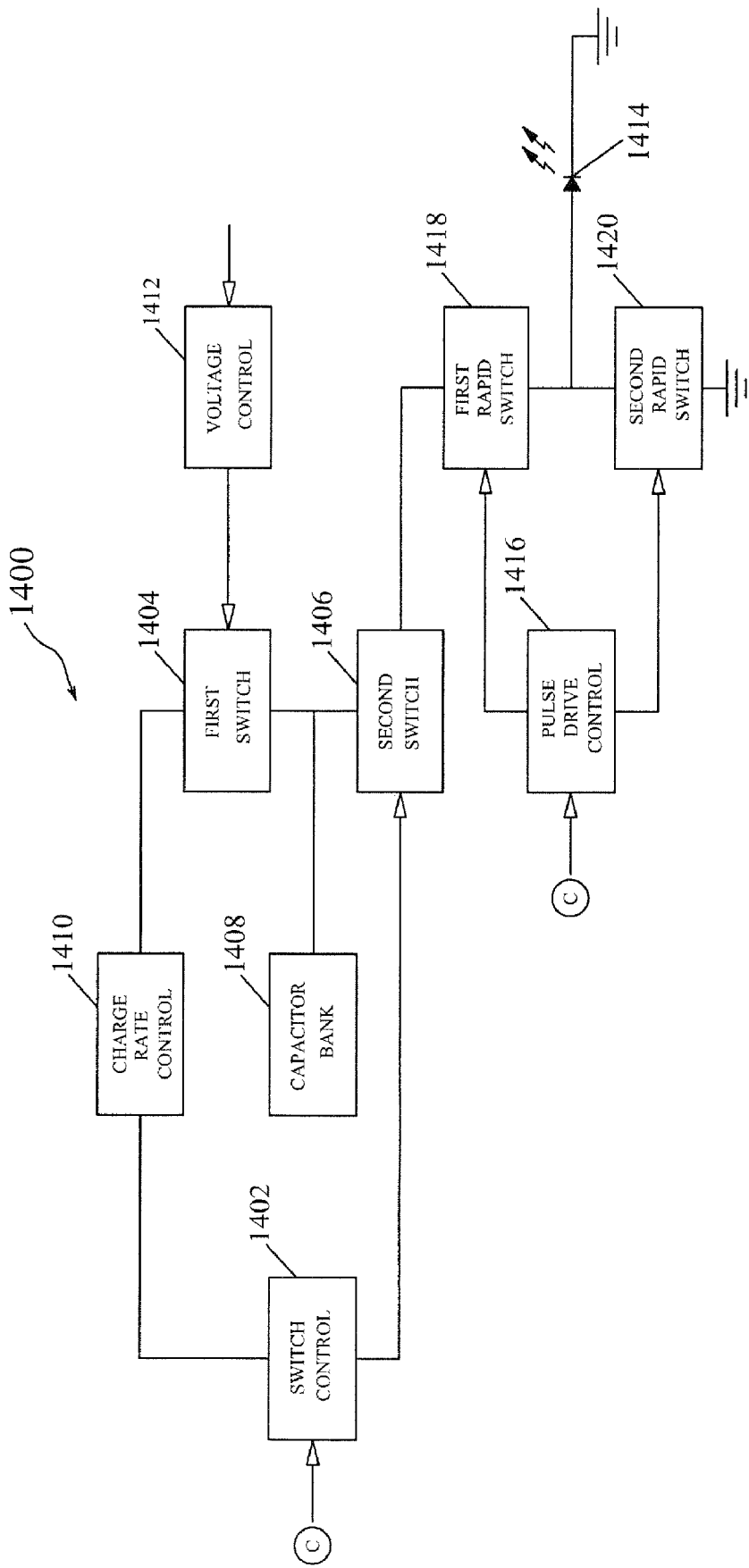
FIG. 14 is a functional block diagram of a control circuit.

In a preferred embodiment, each of the LED light sources are controlled by control circuits, such as control circuit 1400, illustrated in functional block diagram in FIG. 14. A control circuit 1400 may control all or any subset of the LED light sources. Preferably, however, a single control circuit controls two LED devices having the same frequency characteristics and positioned so that the failure of one LED device would not significantly affect the function of the apparatus as a whole. The control circuit 1400 comprises a switch control unit 1402 that selectively opens and closes a first switch circuit 1404 and a second switch circuit 1406 in response to signals from a microprocessor to maintain a selected charge on a bank 1408 of power capacitors. The first switch circuit 1404 is initially closed to charge the capacitor bank 1408 while the second switch circuit 1406 is open. A charging rate control circuit 1410 limits the rate at which charge can be transferred to the capacitor bank 1408. This prevents a sudden current demand as the system is initialized. Such a sudden demand might interfere with other power demands of the system as a whole. The charging rate may be fixed and not programmable, while other parameters of the control circuit 1400 are programmable. The charging rate could be made programmable by using the digital potentiometer that adjusts the voltage stored on the capacitor bank 1408. The microprocessor could then control charging by ramping the setting of the digital potentiometer at the programmed, controlled rate of change.

A voltage control circuit 1412 regulates the peak voltage stored on the capacitor bank 1408. The microprocessor selects the voltage stored on the capacitor bank 1408 and preferably adjusts a digitally controllable device in the voltage control circuit. After the capacitor bank 1408 is charged to its selected voltage, first switch circuit 1404 can be left closed, allowing charging to continue during normal operation, and second switch circuit 1406 can be closed, providing driving power to the LED devices through other circuit components, as explained below. The switch control unit 1402 provides timing and control signals to close the first switch circuit 1404 and to close the second switch circuit 1406. When both switch circuits 1404 and 1406 are closed, power is established within the capacitor bank 1408.

With second switch circuit 1406 closed, power is available to the LED device or devices 1414. Responsive to signals from the microprocessor, a pulse drive controller 1416 controls first rapid response switch 1418 and second rapid response switch 1420, which bracket the LED device 1414. Each of the rapid response switches 1418, 1420 is configured to turn on or off in such a manner to provide a well-defined square power wave to the LED device 1414. With the second rapid response switch open, the first response switch can be closed to provide a path for current from the capacitor bank 1408 through the LED device 1414 to ground. As will be explained more fully below, the leading edge of the wave is well defined and abrupt and the voltage then remains relatively constant because of the substantial size of the capacitors in the capacitor bank 1408. After the selected illumination period, the pulse drive controller 1416 briefly turns off both switches 1418, 1420, as explained above in connection with the first and second switch circuits 1404, 1406, and then opens the second rapid response switch 1420 to ground, draining any remaining power away from the LED device 1414, and sharply and precisely turning the LED device 1414 off.

The control circuit 1400 produces a precisely controlled stroboscopic illumination. Both the duration and the magnitude (voltage) of the LED device output can be digitally controlled. This contrasts with xenon stroboscopic flash tubes, where the light-generating phenomenon is essentially an explosion, with an uncertain duration and an indeterminate intensity. In the preferred application for the present stroboscopic light, the target image is relatively far both from the light source and the detection device (video camera), but the phenomenon being detected, a boundary between fluid layers, is quite subtle. An intense yet consistent illumination is needed. Because the shutter speed of the camera is slower that the phenomenon being observed, the stroboscopic flash serves as the shutter for the optical system, and must, therefore, have both an abrupt beginning and end. These features are provided by the LED light sources and control circuits described herein.

Moreover, in the preferred application of the stroboscopic light, the limiting parameter tends to be the refresh rate for the video camera, which is generally limited to about 25-30 Hz, that is, one image for every second revolution of the rotor. Because this cycle between images is relatively long compared to the period of illumination by the LED light sources, the control circuit 1400 has ample time to fully recharge the capacitor bank 1408 through first and second switch circuits 1404, 1406 before power is supplied to the LED device 1414 through first and second rapid response switches 1418, 1420.

Figure 15:
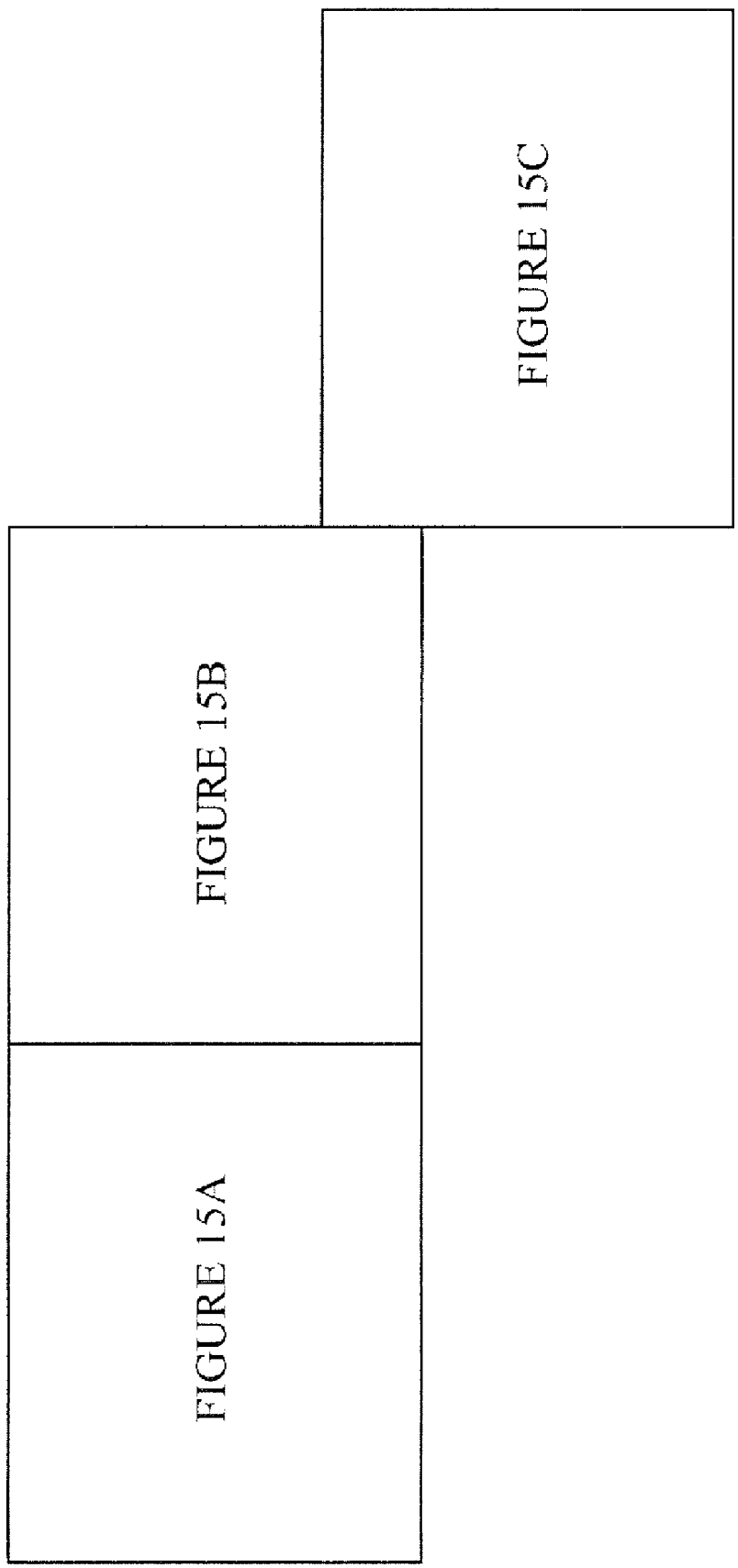
FIG. 15 shows the relationship of FIGS. 15A, 15B and 15C, which are schematic diagrams of the control circuit of FIG. 14.
Figure 15A:
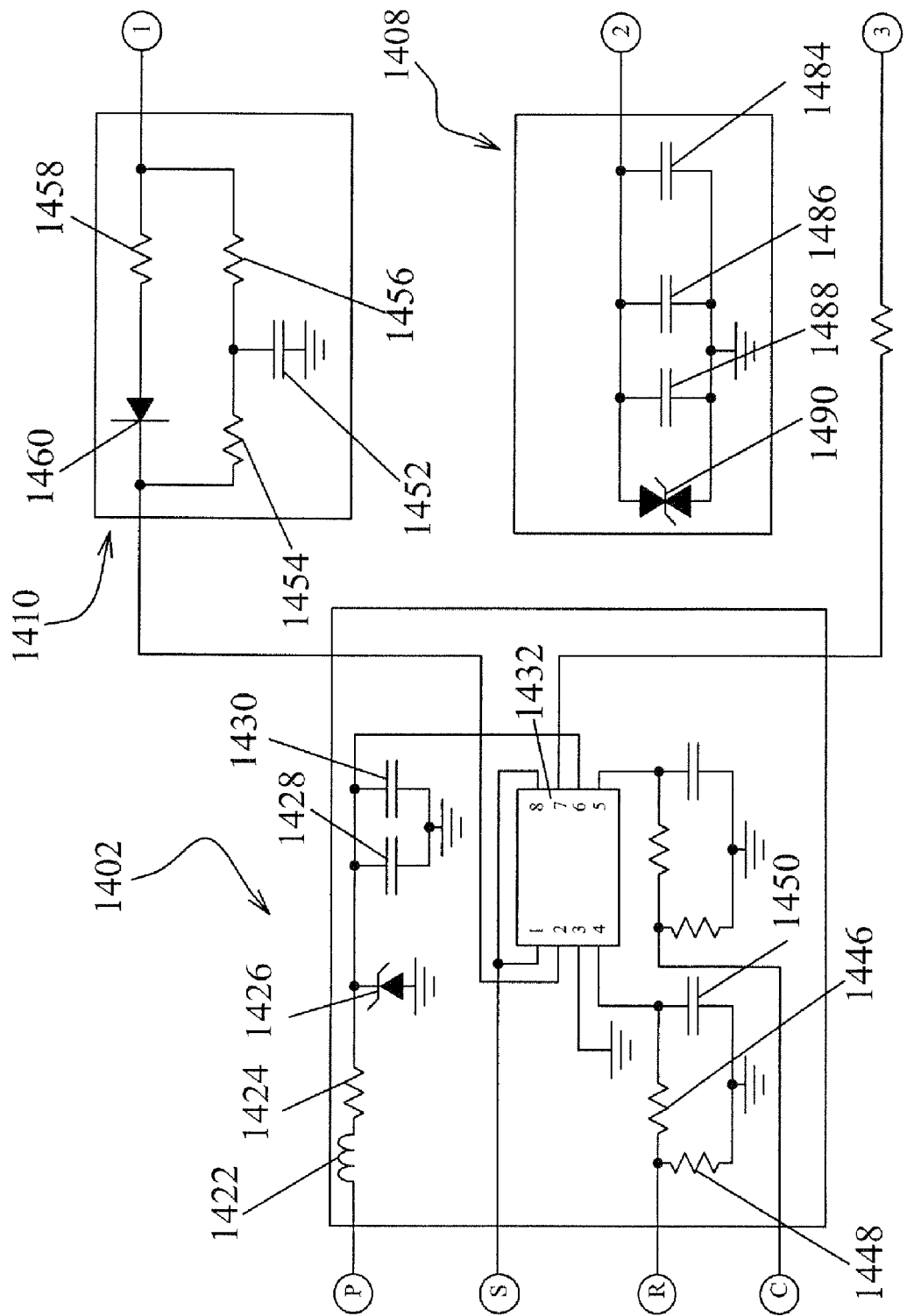
Figure 15B:
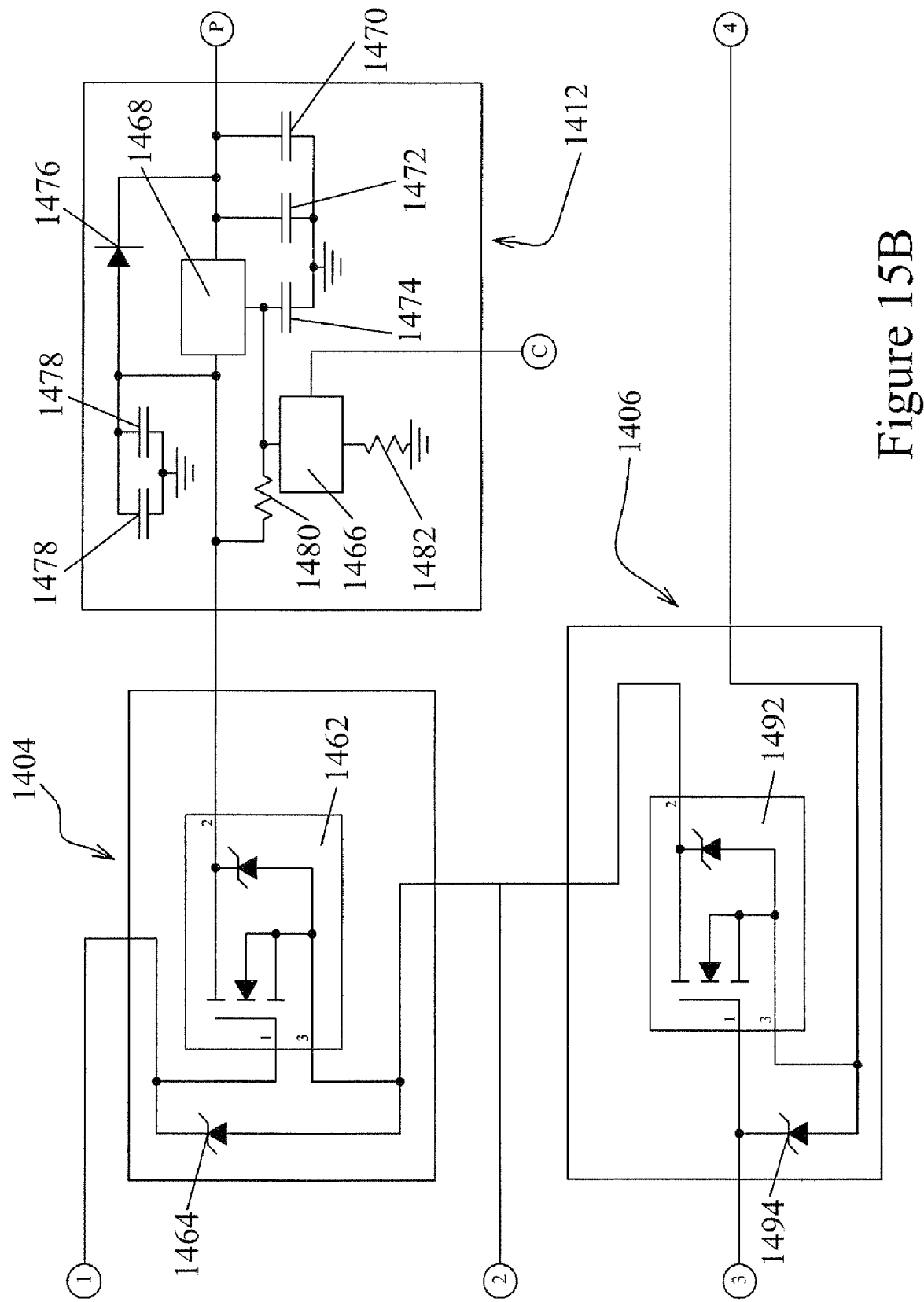
Figure 15C:
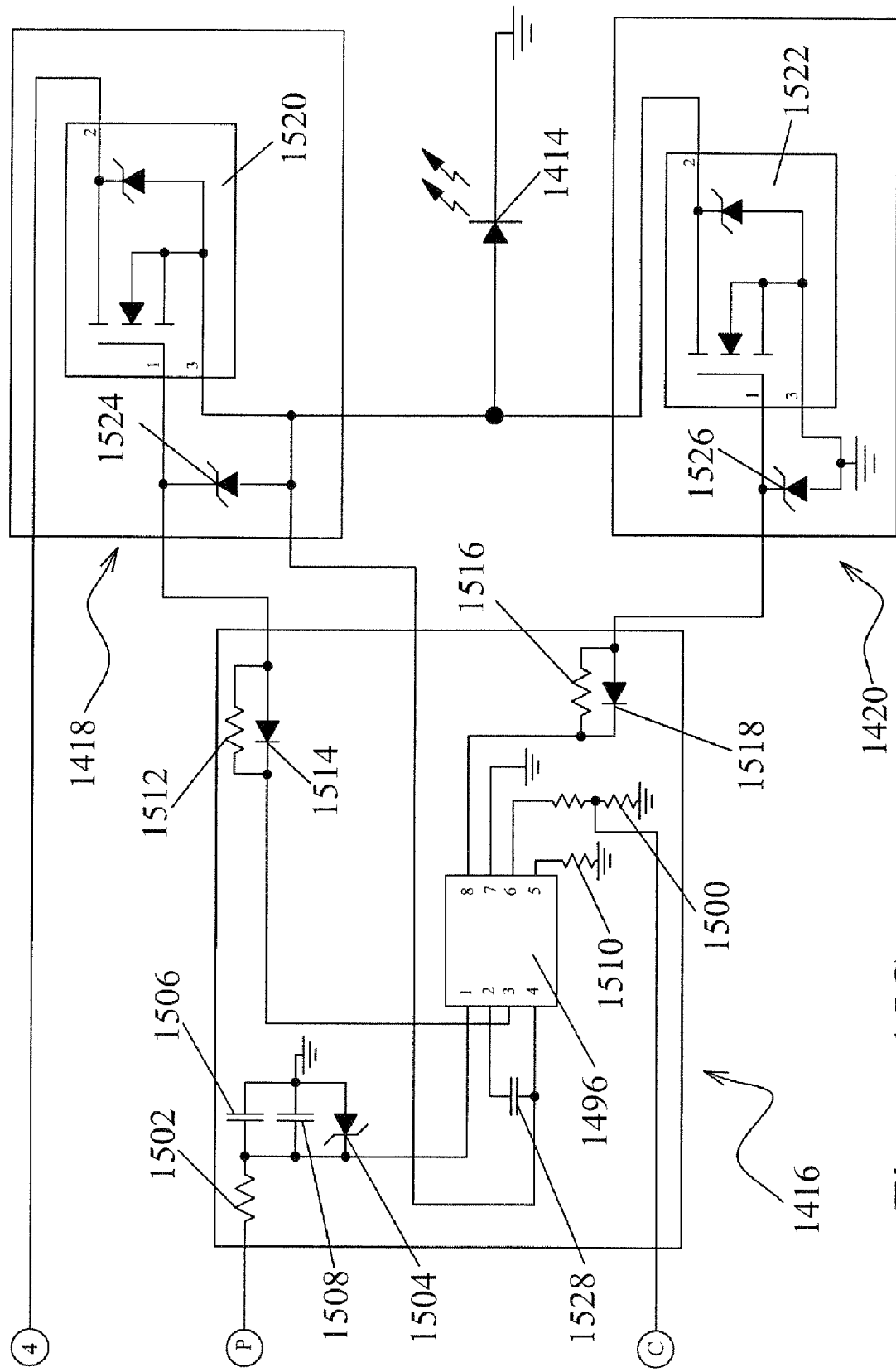

The control circuit 1400 is illustrated in greater detail in FIGS. 15A, 15B, and 15C. The switch control unit 1402 is connected to a power source at P, preferably 24 V. An inductor 1422 provides reverse filtering by preventing high frequency transient electrical signals, produced in the control circuit 1400 when the LED device 1414 is rapidly switched on and off, from propagating back into other parts of the blood processing apparatus. The incoming voltage is regulated through a resistor 1424 and across a Zener diode 1426 and capacitors 1428, 1430, which are connected to ground. One 1428 of the capacitors large enough to smooth fluctuations in the incoming electrical power, while the other capacitor 1430 is about two orders of magnitude smaller and presents a path to ground for the high frequency transients blocked by the inductor 1422. The regulated voltage is connected to the Vs pin, pin 6, of an integrated switching circuit 1432, for example a dual MOSFET driver LTC1255CS8 available from Linear Technology. Pin numbers correspond to the exemplary LTC1255CS8 device. The ground pin, pin 3, of the integrated switching circuit 1432, is connected to system ground. The exemplary switching circuit 1432 provides two MOSFET switching channels.

Such switching channels could be provided by separate integrated circuits or by discrete components. The drain sense pins, pin 1 and pin 8, are both connected to reset circuitry (not shown). Reset circuitry should provide a signal to reset the switching circuit 1432 in response to certain conditions such as inadequate voltage, or initial conditions wherein operational delays are introduced to allow initial transients to settle out. The structure of such reset circuitry is known to those of skill in the art and is dependant on the characteristics of the associated microprocessor, and need not be more fully described here. In the switching circuit 1432, the gate drive pins, pin 2 and pin 7, are driven to ground when a switch is to be turned off or they are driven high when a switch is turned on. Persons skilled in the art will recognize, of course, that circuits using opposite polarity may also be used. The input pins, pin 4 and pin 5, of the present example are active high and, in the exemplary LTC1255 integrated circuit, should be held low during the application of power to properly set an internal input latch. Input pin 4 is connected through a voltage divider circuit comprising resistors 1444, 1446, 1448 and capacitor 1450. A reset circuit (not shown) at connection R keeps input pin 4 low, and the associated MOSFET closed, when adequate power (e.g., 24 V) is not available for an adequate length of time (e.g., longer than 2 seconds). If adequate power is detected, input pin 4 opens gate drive pin 2, and charging of the control circuit 1400 begins. Current flows into the charging rate control circuit 1410 where a large resistor 1454 and capacitor 1452 allow the MOSFET to close in a controlled manner and limit the initial rate of current flowing into the capacitor bank 1408. It is desirable to manage this inrush of current flow into the capacitor bank to prevent an abrupt increase or spike in current could adversely affect other circuits, such as microprocessors or cause power supply or system resetting. A small resistor 1456 (about $\frac{1}{10}$ of the large resistor 1454) is connected in series with the large resistor 1454, the capacitor 1452 being connected between the two resistors 1454, 1456. A return current path is provided through a resistor 1458 and diode 1460, connected in parallel with the above-mentioned large and small resistors 1454, 1456 and capacitor 1452, and is forward biased to discharge the gate of the MOSFET integrated circuit 1462 in the first switch circuit 1404.

A signal from the charging rate control circuit 1410 closes the first switch circuit 1404, allowing current to flow from the voltage control circuit 1412 to the capacitor bank 1408. The first switch circuit 1404 comprises a power MOSFET integrated circuit 1462, for example, an IRFZ44N MOSFET available from International Rectifier, which acts as a switch. The gate of the MOSFET 1462 is coupled to the gate drive pin 2 of the switching circuit 1462 through the charging rate control circuit 1410. The source of the MOSFET is connected to the capacitor bank 1408 and the second switch circuit 1406. The drain of the MOSFET 1462 is connected to the voltage control circuit 1412. A Zener diode 1464 connected across the gate and the source clamps the voltage at the gate to 12 volts.

The voltage control circuit 1412 receives instructions to set the voltage on the capacitor bank 1408 consistent with the voltage requirements of LED devices driven by the circuit 1400. LED devices emitting different wavelengths or colors generally require different voltage levels. The voltage for the particular control circuit 1400 is selected by microprocessors controlling the blood processing apparatus through connection C connected to a digital potentiometer 1466. The potentiometer 1466 controls the adjust pin on an adjustable voltage regulator 1468, for example an LT1085CT available from Linear Technology, by changing the voltage at a location between a first resistor 1480, which is connected to the out pin of the regulator, and the potentiometer 1466 in series with a second resistor 1482, which is connected to system ground. The in pin of the voltage regulator 1468 is connected to the 24-volt power supply P. Capacitors 1470, 1472, and 1474 may filter noise and transients from both the power supply P and the potentiometer 1466, providing stability of performance. The out pin of the regulator 1468 is connected through the drain of the MOSFET 1462 to the capacitor bank 1408. The regulated voltage at the out pin is the maximum voltage to which the capacitor bank can be charged. A reverse biased diode 1476 may be connected between the out pin of the regulator 1468 and the in pin of the regulator to protect the regulator in the event that the capacitor bank is charged, but the connection to the power supply P is interrupted. One or more capacitors 1478 may also be connected to the out pin of the regulator whereby high frequency transient voltages may be conducted to ground.

The capacitor bank 1408 comprises one or more capacitors 1484, 1486, 1488 connected on one side between the first switch circuit 1404 and the second switch circuit 1406 and on the other side to system ground. A bi-directional transient voltage suppressor or "back-to-back" zener diode 1490 may be provided in parallel with the capacitors to provide transient protection for the capacitors, particularly if the rated voltage of the capacitors is close to the maximum voltage available from the power supply. Physically smaller capacitors are desirable due to constraints of space in the preferred application. When the first switch circuit 1404 is closed, the capacitors 1484, 1486, 1488 are charged to the voltage set by the voltage control circuit 1412. When the second switch circuit 1406 is closed, the capacitors 1484, 1486, 1488 are connected to further circuit elements and are ready to provide drive current to the LED device, as more fully explained below.

The second switch circuit 1406 comprises a power MOSFET integrated circuit 1492, for example, an IRFZ44N MOSFET available from International Rectifier, which acts as a switch. The gate of the MOSFET 1492 is coupled to gate drive pin 7 of the switching circuit 1432 in the switch control unit 1402. The drain of the MOSFET is connected to the capacitor bank 1408 and the first switch circuit 1404. The source of the MOSFET 1492 is connected through the first rapid response switch 1418 to the LED device 1414. A Zener diode 1494 connected across the gate and the source clamps the voltage at the gate to 12 volts.

Electric power delivered from the capacitor bank 1408 through the second switch circuit 1406 to the LED device 1414, as connected through first rapid response switch 1418, is controlled by the pulse drive controller 1416, which selectively opens and closes the first rapid response switch 1418 and the second rapid response switch 1420, allowing current to flow into and out of LED device 1414. The pulse drive controller 1416 comprises a half-bridge gate driver 1496, such as an LM5104 integrated circuit from National Semiconductor. The gate driver 1496 receives signals from the microcomputer C at an input pin 6. A resistor 1498 in series with the computer input and the input pin 6 limits the current at the pin. Another resister 1500 connected to the computer input and to system ground holds the voltage at the input pin 6 low in the absence of a control pulse from the computer. The VDD or voltage in pin 1 of the gate driver 1496 receives electrical power for the gate driver through a voltage regulator comprising a resistor 1502 and 12-volt Zener diode 1504 connected in series between the power supply P and system ground. One or more capacitors 1506, 1508 may be connected in parallel with the Zener diode to conduct high frequency transients to ground. The gate driver is grounded through Vss pin 7. A resistor 1510 connecting the deadtime programming pin 5 to system ground sets a delay between high and low transitions in the gate driver. This delay prevents the gate driver from closing the first rapid response switch 1418 and the second rapid response switch at the same time, which would short the capacitor bank to ground. In response to a signal from the computer C, the gate driver 1496 produces a signal at high out pin 3. The signal passes through a resistor 1512, which damps the turn-on characteristics of the first rapid response switch 1418 and controls voltage spikes and generation of radiated electrical interference as the first rapid response switch is closed. The gate of MOSFET 1418 may discharge through diode 1514 in parallel with resistor 1512. As the signal from the computer C ends, the gate driver 1496 produces a signal at low out pin 8. This signal also passes through a resistor 1516, which damps the turn-on characteristics of the second rapid response switch 1420 and controls voltage spikes and generation of radiated electrical interference as the second rapid response switch is closed. The gate of MOSFET 1522 may discharge through diode 1518 in parallel with resistor 1516. The second rapid response switch 1420 is normally "on" or "closed", except when a pulse is produced. In contrast, first rapid response switch 1418 is normally "off" or "open". Thus, in the exemplary embodiment, when the signal from a microprocessor through C is low, switch 1418 is off, while switch 1420 is on, and the LED device 1414 produces no light. As the signal from the microprocessor through C goes high, both switches 1418, 1420 are momentarily open or off. As the output at C remains high, switch 1418 turns on (closes), while switch 1420 stays open or off. The LED device produces light. As the signal from the microprocessor returns to low, both switches 1418, 1420 are again momentarily open or off. Switch 1420 then turns on or closes, and the LED device discharges to ground. One skilled in the art will recognize that the polarity of the signals, the states of the switches, and the direction of current flow through the LED device could be reversed without departing from the teachings of the present invention.

Both the first rapid response switch 1418 and the second rapid response switch 1420 are comprised of a power MOSFET 1520, 1522, for example an IRFZ44N MOSFET available from international Rectifier, with a Zener diode 1524, 1526 connected across the gate and the source of the respective power MOSFET as a voltage clamp for the respective gate of the MOSFET 1520, 1522. The drain of the MOSFET 1520 of the first rapid response switch 1418 is connected to the second switch circuit 1406, as described above. When the capacitor bank is charged and the second switch circuit 1406 is closed, the signal to the gate of the MOSFET 1520 from the gate driver 1496 causes the MOSFET 1520 to conduct power from the MOSFET source through the LED device 1414 to ground. The MOSFET source is also connected to a high side MOSFET source connection pin 4 on the gate driver 1496. A bootstrap capacitor 1528 connects the source connection pin 4 to a bootstrap rail pin 2 of the gate driver 1496. When the signal from the computer C ends, the gate driver 1496 initially both opens the rapid response switch 1418 and leaves the second response switch 1420 open for a very brief time (on the order of nanoseconds, as adaptively controlled by gate driver 1496), thereby preventing a short circuit from the capacitor bank to system ground. The gate driver 1496 then provides a signal to the gate of the MOSFET 1522 in the second rapid response switch 1420, causing the MOSFET 1522 to conduct to system ground. Any power energizing the LED device 1414 is conducted away from the LED device to ground. A sharp, well-controlled square-wave voltage, with well-defined leading and trailing edges, can thereby be produced on the LED device, so that the duration and magnitude of illuminations produced by the LED device are consistent.

Preferably, each control circuit 1400 controls an LED device or devices of a single type or output frequency. The LED device may produce illumination in the visible or invisible regions of the spectrum, such as red, green or infrared light or full-spectrum white light, as may be appropriate for the desired application. Preferably, two LED devices may be connected in parallel, reducing the cost, size and complexity of the drive circuits. In addition, failure of one of the LED devices would not completely incapacitate a specific control circuit.

Figure 16:
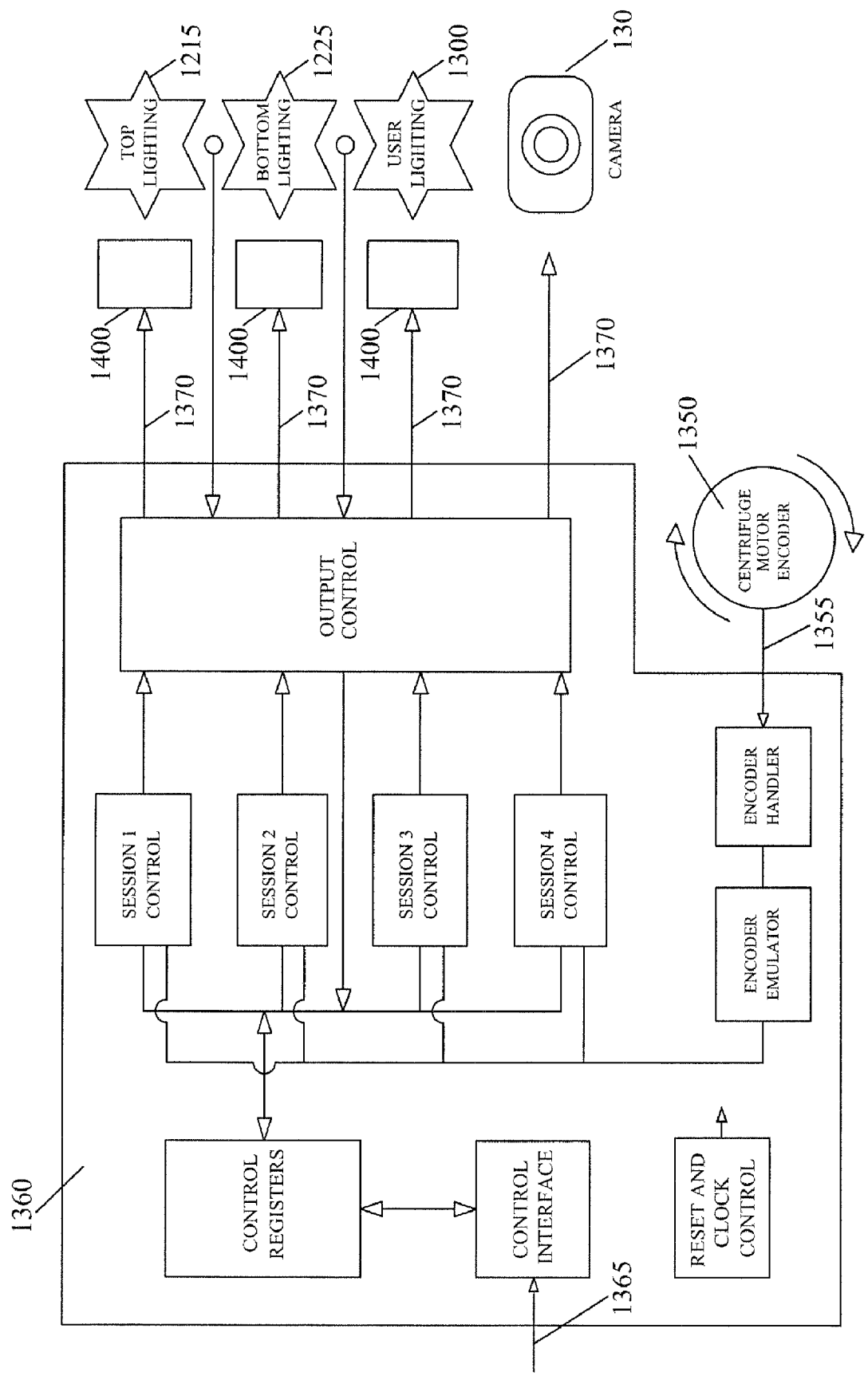
FIG. 16 shows a functional flow diagram representing a method of synchronizing light pulses generated by top and bottom pulsed LED light sources trigger and trigger delay settings.

FIG. 16 shows a functional flow diagram representing a method of synchronizing light pulses generated by top, bottom and user observation pulsed LED light sources and camera shutter and gate settings. As illustrated in FIG. 16, encoded motor system 1350 generates one or more output signals 1355 corresponding to the rotational position of the optical cell. Output signals 1355 are received as input to the synchronization and timing controller 1360. Synchronization and timing controller 1360 is also configured to receive control signals 1365 from a device controller. Control signals 1365 and output signals 1355 are processed by synchronization and timing controller 1360, and serve as the basis of a plurality of trigger signals 1370 which are sent to the top pulsed LED light source, the bottom pulsed LED light source and the CCD camera. Optionally, one or more trigger signals may also be used to adjust the lighting in the density centrifuge chamber to allow a user to visually assess the state of the density centrifuge during processing. An advantage of this aspect of the present invention is that timing and synchronization of light pulses and camera settings are handled by the synchronization and timing controller 1360 without expenditure of other system resources, such as processing time of the device controller.

Use of LED light sources in the present invention is beneficial because these light sources are small, light weight and have relatively low power consumptions compared to many conventional non-LED light sources. LED light sources also exhibit long operating lifetimes, high efficiency and uniform intensity with little generated heat. In addition, LED light sources are capable of pulse operation generating discrete pulse having accurately selectable temporal characteristics such as pulse width and initiation time. Pulse LED sources also are capable of generating pulses having substantially uniform intensities and wavelength distributions. Use of LED is also preferred for some applications of the present invention because it provides good control of the wavelength distribution of the upper and/or lower illumination beams. The present invention includes embodiments, wherein the wavelength distribution of top and bottom illumination beams is selectively adjustable by mixing the output of LEDs having different colors, such as red, green and white LEDs and independently controlling the duration of illuminations of the different colors or wavelengths. In these embodiments, the wavelength distributions of top and bottom illumination beams may be independently selected on a shot per shot basis to optimize a desired optical measurement, such as the measurement of the position of phase boundaries between optically differentiable blood components and/or the compositions of extracted blood components passing through an extraction port.

We claim:

1. A stroboscopic apparatus comprising:
   a light source for providing an incident light beam for illuminating an observation region, said light source comprising
      a plurality of reflective surfaces spaced around a central illumination axis, and
      a plurality of light emitting diodes, at least one light emitting diode being spaced away from said central illumination axis radially outward from at least one of said reflective surfaces such that light from said diode is reflected from said surface generally along said central axis;
   a controller energizing said diodes for selected periods of time, said controller produces pulses for energizing said diodes, said pulses having a variable duration and amplitude for providing a consistent light intensity output from said diodes, and
   a light collection element for collecting at least a portion of said light transmitted, scattered or both from said observation region.

2. The apparatus of claim 1 wherein said light source further comprises at least three reflective surfaces, each surface being generally triangular and the surfaces meeting at a common vertex near said central illumination axis, and wherein at least one light emitting diode is spaced radially outward from each reflective surface, said diodes being substantially radially equidistant from said central illumination axis.

3. The apparatus of claim 2 wherein said light source comprises at least six reflective surfaces and at least six light emitting diodes.

4. The apparatus of claim 1 wherein said reflective surfaces are parabolic segments having generally triangular perimeters and wherein at least one of said light emitting diodes is located near a focal point of each of said parabolic segments.

5. The apparatus of claim 1 wherein said controller is a digital controller.

6. The apparatus of claim 1 wherein said controller comprises a power capacitor in electrical communication with at least one of said diodes and a charge control circuit in electrical communication with a power supply, said charge control circuit controlling the rate of charging of said power capacitor.

7. The apparatus of claim 1 wherein said controller comprises a pair of switches connected in series, at least one light emitting diode being connected between said switches.

8. The apparatus of claim 7 further comprising a circuit for closing a first switch of said pair of switches when a second switch of said pair of switches is open and closing said second switch when said first switch is open.

9. The apparatus of claim 8 wherein said light emitting diode is connected to ground through at least one of said switches at the end of a period of illumination by said at least one diode.

10. The apparatus of claim 1 further comprising at least one additional light source, said additional light source comprising at least one light emitting diode having a light emitting plate, and a modified parabolic reflector surrounding said light emitting diode, said parabolic reflector having walls spaced radially outwardly from a central axis of symmetry such that a focal point of a radial segment of said parabolic reflector falls radially outwardly from a center of said plate, and such that all such focal points form a circular focal area on said plate.

11. A stroboscopic apparatus comprising:
    a light source for providing an incident light beam for illuminating an observation region, said light source comprising at least one light emitting diode;
    a controller energizing said diode for selected periods of time, said controller produces pulses for energizing said diode, said pulses having a variable duration and amplitude for providing a consistent light intensity output from said diodes, and said controller comprising a pair of switches connected in series, said at least one light emitting diode being connected between said switches.

12. The apparatus of claim 11 further comprising a circuit for closing a first switch of said pair of switches when a second switch of said pair of switches is open and closing said second switch when said first switch is open.

13. The apparatus of claim 12 wherein said light emitting diode is connected to ground through at least one of said switches at the end of a period of illumination by said at least one diode.

14. The apparatus of claim 11 wherein said light emitting diode is connected to ground through at least one of said switches at the end of a period of illumination by said at least one diode.

* * * * *